(12) United States Patent
Law et al.

(10) Patent No.: US 7,547,544 B2
(45) Date of Patent: Jun. 16, 2009

(54) ANTIBODIES AGAINST GPR64 AND USES THEREOF

(75) Inventors: Debbie Law, San Francisco, CA (US); Qi Wang, Munich (DE); Robert DuBridge, Belmont, CA (US); Vinay Bhaskar, San Francisco, CA (US)

(73) Assignee: Facet Biotech Corporation, Redwood City, CA (US)

( * ) Notice: Subject to any disclaimer, the term of this patent is extended or adjusted under 35 U.S.C. 154(b) by 151 days.

(21) Appl. No.: 11/852,155

(22) Filed: Sep. 7, 2007

(65) Prior Publication Data

US 2008/0107642 A1     May 8, 2008

Related U.S. Application Data

(62) Division of application No. 10/741,657, filed on Dec. 19, 2003, now Pat. No. 7,276,372.

(60) Provisional application No. 60/435,618, filed on Dec. 20, 2002.

(51) Int. Cl.
 *C12N 5/20* (2006.01)

(52) U.S. Cl. ................. 435/331; 530/387.1; 530/387.3; 530/387.9; 530/388.8; 530/391.3; 530/391.7

(58) Field of Classification Search ............... 530/387.1, 530/387.3, 387.9, 388.8, 391.3, 391.7; 435/331
See application file for complete search history.

(56) References Cited

U.S. PATENT DOCUMENTS

| 6,183,968 | B1 | 2/2001 | Bandman |
| 2002/0142951 | A1 | 10/2002 | Webster |
| 2004/0005563 | A1 | 1/2004 | Mack |

FOREIGN PATENT DOCUMENTS

| DE | 19617940 A1 | 10/1997 |
| EP | 0805204 | 11/1997 |
| EP | 1033401 | 9/2000 |
| WO | 9845436 A2 | 10/1998 |
| WO | 0034473 A2 | 6/2000 |
| WO | 0056881 A1 | 9/2000 |
| WO | 0154477 A2 | 8/2001 |
| WO | 0170979 A2 | 9/2001 |
| WO | 0210449 A2 | 2/2002 |
| WO | 0261087 A2 | 8/2002 |
| WO | 0279406 A2 | 10/2002 |
| WO | 0283856 A2 | 10/2002 |
| WO | 02101357 A2 | 12/2002 |
| WO | 02102235 A2 | 12/2002 |
| WO | WO02102235 A2 | 12/2002 |
| WO | 03038129 A2 | 5/2003 |
| WO | 03051925 A1 | 6/2003 |
| WO | 03071272 A1 | 8/2003 |
| WO | 2004037860 A1 | 5/2004 |

OTHER PUBLICATIONS

Osterhoff et al., "Cloning of a human epididymis-specific mRNA, HE6, encoding a novel member of the seven transmembrane-domain receptor superfamily," DNA and Cell Biology, 16:379-389 (1997).
Obermann et al., "HE6, a two-subunit heptahelical receptor associated with apical membranes of efficient epididymal duct epithelia," Molec. Reprod. & Develop. 64:13-26 (2003).
Gilewski et al., "Vaccination of high-risk breast cancer patients with mucin-1 (MUC1) keyhole limpet hemocyanin conjugate plus QS-21," Clin. Cancer Res. 6:1693-1701 (2000).
Scholl et al., "Recombinant vaccinia virus encoding human MUC1 and IL2 as immunotherapy in patients with breast cancer," J. Immunother. 23:570-580 (2000).
Bon et al., "Clinical and technical evaluation of ACS BR serum assay of MUC1 gene-derived glycoprotein in breast cancer, and comparison with CA 15-3 assays," Clin. Chem. 43:585-593 (1997).
Fitzgibbons et al., "Prognostic factors in breast cancer. College of American Pathologists Consensus Statement 1999," Arch. Pathol. Lab. Med. 124:966-978 (2000).
Hamilton and Piccart, "The contribution of molecular markers to the prediction of response in the treatment of breast cancer: a review of the literature on HER-2, p53 and BCL-2," Ann. Oncol. 11:647-663 (2000).
Robson, "Are BRCA1 and BRCA2-associated breast cancers different? Prognosis of BRCA-1 associated breast cancer," J. Clin. Oncol. 18(21 Suppl):113S-118S (2000).
Fredriksson R., et al., "Novel human G protein-coupled receptors with long N-terminal containing GPS domains and Ser/Thr-rich regions," FEBs Letters 531:407-414 (2002).
Genbank accession CAA57479 (1996).
Genbank accession X81892 (1996).
Doronina et al., "Development of potent monoclonal antibody auristatin conjugates for cancer therapy," Nature Biotech, 21(7):778-784 (Jul. 2003).
Delphion Record for EP0805204B1 (Nov. 2006).
Toki et al., "Cures and regressions of established tumor xenografts with monoclonal antibody auristatin E conjugates," ACS National Meeting, No. 223rd, p. 1, abstract (Apr. 7, 2002).

*Primary Examiner*—Stephen L Rawlings
(74) *Attorney, Agent, or Firm*—DLA Piper LLP (US)

(57) ABSTRACT

GPR64 antibody compositions are provided. These antibodies may be used for diagnosis or treatment of cancer, especially ovarian cancer, Ewing's sarcoma, uterine cancer, and other GPR64 expressing tumor types.

18 Claims, 15 Drawing Sheets

```
1          11         21         31         41         51
|          |          |          |          |          |
AGCCAGCCCG AGGACGCGAG CGGCAGGTGT GCACAGAGGT TCTCCACTTT GTTTTCTGAA    60
CTCGCGGTCA GGATGGTTTT CTCTGTCAGG CAGTGTGGCC ATGTTGGCAG AACTGAAGAA   120
GTTTTACTGA CGTTCAAGAT ATTCCTTGTC ATCATTTGTC TTCATGTCGT TCTGGTAACA   180
TCCCTGGAAG AAGATACTGA TAATTCCAGT TTGTCACCAC CACCTGCTAA ATTATCTGTT   240
GTCAGTTTTG CCCCCTCCTC CAATGAGGTT GAAACAACAA GCCTCAATGA TGTTACTTTA   300
AGCTTACTCC CTTCAAACGA AACAGAAAAA ACTAAAATCA CTATAGTAAA AACCTTCAAT   360
GCTTCAGGCG TCAAACCCCA GAGAAATATC TGCAATTTGT CATCTATTTG CAATGACTCA   420
GCATTTTTTA GAGGTGAGAT CATGTTTCAA TATGATAAAG AAAGCACTGT TCCCCAGAAT   480
CAACATATAA CGAATGGCAC CTTAACTGGA GTCCTGTCTC TAAGTGAATT AAAACGCTCA   540
GAGCTCAACA AAACCCTGCA AACCCTAAGT GAGACTTACT TTATAATGTG TGCTACAGCA   600
GAGGCCCAAA GCACATTAAA TTGTACATTC ACAATAAAAC TGAATAATAC AATGAATGCA   660
TGTGCTGCAA TAGCCGCTTT GGAAAGAGTA AAGATTCGAC CAATGGAACA CTGCTGCTGT   720
TCTGTCAGGA TACCCTGCCC TTCCTCCCCA GAAGAGTTGG GAAAGCTTCA GTGTGACCTG   780
CAGGATCCCA TTGTCTGTCT TGCTGACCAT CCACGTGGCC CACCATTTTC TTCCAGCCAA   840
TCCATCCCAG TGGTGCCTCG GGCCACTGTG CTTTCCCAGG TCCCCAAAGC TACCTCTTTT   900
GCTGAGCCTC CAGATTATTC ACCTGTGACC CACAATGTTC CCTCTCCAA T AGGGGAGATT   960
CAACCCCTTT CACCCCAGCC TTCAGCTCCC ATAGCTTCCA GCCTGCCAT TGACATGCCC  1020
CCACAGTCTG AAACGATCTC TTCCCCTATG CCCAAACCC ATGTCTCCGG CACCCCACCT  1080
CCTGTGAAAG CCTCATTTTC CTCTCCCACC GTGTCTGCCC CTGCGAATGT CAACACTACC  1140
AGCGCACCTC CTGTCCAGAC AGACATCGTC AACACCAGCA GTATTTCTGA TCTTGAGAAC  1200
CAAGTGTTGC AGATGGAGAA GGCTCTGTCC TTGGGCAGCC TGGAGCCTAA CCTCGCAGGA  1260
GAAATGATCA ACCAAGTCAG CAGACTCCTT CATTCCCCGC CTGACATGCT GGCCCCTCTG  1320
GCTCAAAGAT TGCTGAAAGT AGTGGATGAC ATTGGCCTAC AGCTGAACTT TTCAAACACG  1380
ACTATAAGTC TAACCTCCCC TTCTTTGGCT CTGGCTGTGA TCAGAGTGAA TGCCAGTAGT  1440
TTCAACACAA CTACCTTTGT GGCCCAAGAC CCTGCAAATC TTCAGGTTTC TCTGGAAACC  1500
CAAGCTCCTG AGAACAGTAT TGGCACAATT ACTCTTCCTT CATCGCTGAT GAATAATTTA  1560
CCAGCTCATG ACATGGAGCT AGCTTCC AGG GTTCAGTTCA ATTTTTTTGA AACACCTGCT  1620
TTGTTTCAGG ATCCTTCCCT GGAGAACCTC TCTCTGATCA GCTACGTCAT ATCATCGAGT  1680
GTTGCAAACC TGACCGTCAG GAACTTGACA AGAAACGTGA CAGTCACATT AAAGCACATC  1740
AACCCGAGCC AGGATGAGTT AACAGTGAGA TGTGTATTTT GGGACTTGGG CAGAAATGGT  1800
GGCAGAGGAG GCTGGTCAGA CAATGGCTGC TCTGTCAAAG ACAGGAGATT GAATGAAACC  1860
ATCTGTACCT GTAGCCATCT AACAAGCTTC GGCGTTCTGC TGGACCTATC TAGGACATCT  1920
GTGCTGCCTG CTCAAATGAT GGCTCTGACG TTCATTACAT ATATTGGTTG TGGGCTTTCA  1980
TCAATTTTTC TGTCAGTGAC TCTTGTAACC TACATAGCTT TTGAAAAGAT CCGGAGGGAT  2040
TACCCTTCCA AAATCCTCAT CCAGCTGTGT GCTGCTCTGC TTCTGCTGAA CCTGGTCTTC  2100
CTCCTGGACT CGTGGATTGC TCTGTATAAG ATGCAAGGCC TCTGCATCTC AGTGGCTGTA  2160
TTTCTTCATT ATTTTCTCTT GGTCTCATTC ACATGGATGG CCTAGAAGC ATTCCATATG  2220
TACCT GGCCC TTGTCAAAGT ATTTAATACT TACATCCGAA ATACATCCT TAAATTCTGC  2280
ATTGTCGGTT GGGGGGTACC AGCTGTGGTT GTGACCATCA TCCTGACTAT ATCCCAGAT  2340
AACTATGGGC TTGGATCCTA TGGGAAATTC CCCAATGGTT CACCGGATGA CTTCTGCTGG  2400
ATCAACAACA ATGCAGTATT CTACATTACG GTGGTGGGAT ATTTCTGTGT GATATTTTG  2460
CTGAACGTCA GCATGTTCAT TGTGGTCCTG GTTCAGCTCT GTCGAATTAA AAAGAAGAAG  2520
CAACTGGGAG CCCAGCGAAA AACCAGTATT CAAGACCTCA GGAGTATCGC TGGCCTTACA  2580
TTTTTACTGG GAATAACTTG GGGCTTTGCC TTCTTTGCCT GGGGACCAGT TAACGTGACC  2640
TTCATGTATC TG TTTGCCAT CTTTAATACC TTACAAGGAT TTTTCATATT CATCTTTTAC  2700
```

FIG. 1

```
TGTGTGGCCA AAGAAAATGT CAGGAAGCAA TGGAGGCGGT ATCTTTGTTG TGGAAAGTTA 2760
CGGCTGGCTG AAAATTCTGA CTGGAGTAAA ACTGCTACTA ATGGTTTAAA GAAGCAGACT 2820
GTAAACCAAG GAGTGTCCAG CTCTTCAAAT TCCTTACAGT CAAGCAGTAA CTCCACTAAC 2880
TCCACCACAC TGCTAGTGAA TAATGATTGC TCAGTACACG CAAGCGGGAA TGGAAATGCT 2940
TCTACAGAGA GGAATGGGGT CTCTTTTAGT GTTCAGAATG GAGATGTGTG CCTTCACGAT 3000
TTCACTGGAA AACAGCACAT GTTTAACGAG AAGGAAGATT CCTGCAATGG GAAAGGCCGT 3060
ATGGCTCTCA GAAGGACTTC AAAGCGGGGA AGCTTACACT TTATTGAGCA AATGTGATTC 3120
CTTTCTTCTA AAATCAAAGC ATGATGCTTG ACAGTGTGAA ATGTCCAATT TTACCTTTTA 3180
CACAATGTGA GATGTATGAA AATCAACTCA TTTTATTCTC GGCAACATCT GGAGAAGCAT 3240
AAGCTAATTA AGGGCGATGA TTATTATTAC AAGAAGAAAC CAAGACATTA CCCATGGTT  3300
TTTAGACATT TCTGATTTGG TTTCTTATCT TTCATTTTAT AAGAAGGTTG GTTTAAACA  3360
ATACACTAAG AATGACTCCT ATAAAGAAAA CAAAAAAGG TAGTGAACTT TCAGCTACCT  3420
TTTAAAGAGG CTAAGTTATC TTTGATAACA TCATATAAAG CAACTGTTGA CTTCAGCCTG 3480
TTGGTGAGTT TAGTTGTGCA TGCCTTTGTT GTATATAAGC TAAATTCTAG TGACCCATGT 3540
GTCAAAAATC TTACTTCTAC ATTTTTTTGT ATTTATTTTC TACTGTGTAA ATGTATTCCT 3600
TTGTAGAATC ATGGTTGTTT TGTCTCACGT GATAATTCAG AAAATCCTTG CTCGTTCCGC 3660
AAATCCTAAA GCTCCTTTTG GAGATGATAT AGGATGTGAA ATACAGAAAC CTCAG TGAAA 3720
TCAAGAAATA ATGATCCCAG CCAGACTGAG AAAATGTAAG CAGACAGTGC CACAGTTAGC 3780
TCATACAGTG CCTTTGAGCA AGTTAGGAAA AGATGCCCCC ACTGGGCAGA CACAGCCCTA 3840
TGGGTCATGG TTTGACAAAC AGAGTGAGAG ACCATATTTT AGCCCCACTC ACCCTCTTGG 3900
GTGCACGACC TGTACAGCCA ACACAGCAT CCAATATGAA TACCCATCCC CTGACCGCAT 3960
CCCCAGTAGT CAGATTATAG AATCTGCACC AAGATGTTTA GCTTTATACC TTGGCCACAG 4020
AGAGGGATGA ACTGTCATCC AGACCATGTG TCAGGAAAAT TGTGAACGTA GATGAGGTAC 4080
ATACACTGCC GCTTCTCAAA TCCCCAGAGC CTTTAGGAAC AGGAGAGTAG ACTAGGATTC 4140
CTTCTCTTAA AAAGGTACAT ATATATGGAA AAAAATCATA TTGCCGTTCT TTAAAAGGCA 4200
ACTGCATGGT ACATTGTTGA TTGTTATGAC TGGTACACTC TGGCCCAGCC AGAGCTATAA 4260
TTGTTTTTTA AATGTGTCTT GAAGAATGCA CAGTGACAAG GGGAGTAGCT ATTGGGAACA 4320
GGGAACTGTC CTACACTGCT ATTGTTGCTA CAT GTATCGA GCCTTGATTG CTCCTAGTTA 4380
TATACAGGGT CTATCTTGCT TCCTACCTAC ATCTGCTTGA GCAGTGCCTC AAGTACATCC 4440
TTATTAGGAA CATTTCAAAC CCCTTTTAGT TAAGTCTTTC ACTAAGGTTC TCTTGCATAT 4500
ATTTCAAGTG AATGTTGGAT CTCAGACTAA CCATAGTAAT AATACACATT TCTGTGAGTG 4560
CTGACTTGTC TTTGCAATAT TTCTTTTCTG ATTTATTTAA TTTTCTTGTA TTTATATGTT 4620
AAAATCAAAA ATGTTAAAAT CAATGAAATA AATTTGCAGT TAAGA
```

GPR64 AMINO ACID SEQUENCE (SEQ ID NO:2)
Gene name:                    G protein-coupled receptor 64
Unigene number:               Hs.421137
Protein Accession #:          NP_005747.1
Signal sequence:              1-38
GPS domain:                   564-615
Transmembrane domains:        624-646, 660-682, 688-710, 733-755, 783-805, 828-850, 858-880
Cellular Localization:        plasma membrane

```
1          11         21         31         41         51
|          |          |          |          |          |
MVFSVRQCGH VGRTEEVLLT FKIFLVIICL HVVLVTSLEE DTDNSSLSPP PAKLSVVSFA  60
PSSNEVETTS LNDVTLSLLP SNETEKTKIT IVKTFNASGV KPQRNICNLS SICNDSAFFR 120
GEIMFQYDKE STVPQNQHIT NGTLTGVLSL SELKRS ELNK TLQTLSETYF IMCATAEAQS 180
TLNCTFTIKL NNTMNACAAI AALERVKIRP MEHCCCSVRI PCPSSPEELG KLQCDLQDPI 240
VCLADHPRGP PFSSSQSIPV VPRATVLSQV PKATSFAEPP DYSPVTHNVP SPIGEIQPLS 300
PQPSAPIASS PAIDMPPQSE TISSPMPQTH VSGTPPPVKA SFSSPTVSAP ANVNTTSAPP 360
VQTDIVNTSS ISDLENQVLQ MEKALSLGSL EPNLAGEMIN QVSRLLHSPP DMLAPLAQRL 420
LKVVDDIGLQ LNFSNTTISL TSPSLALAVI RVNASSFNTT TFVAQDPANL QVSLETQAPE 480
NSIGTITLPS SLMNNLPAHD MELASRVQFN FFETPALFQD PSLENLSLIS YVISSSVANL 540
```

FIG. 1 (Con't.)

```
TVRNLTRNVT VTLKHINPSQ DELTVRC VFW DLGRNGGRGG WSDNGCSVKD RRLNETICTC    600
SHLTSFGVLL DLSRTSVLPA QMMALTFITY IGCGLSSIFL SVTLVTYIAF EKIRRDYPSK    660
ILIQLCAALL LLNLVFLLDS WIALYKMQGL CISVAVFLHY FLLVSFTWMG LEAFHMYLAL    720
VKVFNTYIRK YILKFCIVGW GVPAVVVTII LTISPDNYGL GSYGKFPNGS PDDFCWINNN    780
AVFYITVVGY FCVIFLLNVS MFIVVLVQLC RIKKKKQLGA QRKTSIQDLR SIAGLTFLLG    840
ITWGFAFFAW GPVNVTFMYL FAIFNTLQGF FIFIFYCVAK ENVRKQWRRY LCCGKLRLAE    900
NSDWSKTATN GLKKQTVNQG VSSSSNSLQS SSNSTNSTTL LVNNDCSVHA SGNGNASTER    960
NGVSFSVQNG DVCLHDFTGK QHMFNEKEDS CNGKGRMALR RTSKRGSLHF IEQM
```

FIG. 1 (Con't.)

NUCLEOTIDE AND AMINO ACID SEQUENCES OF GPR64 ANTIBODY CLONES (CDR regions are shown bolded and underlined.)

NUCLEOTIDE SEQUENCES

SEQ ID NO:3: GPR64-1 Heavy Chain Variable Region:

GATGTGCAGCTTCAGGAGTCGGGACCTGGCCTGGTGAAACCTTCTCAGTCTCTG
TCCCTCACCTGCACTGTCACT**GGCTACTCAATCACCAGTGATTATGCCTGGAA
CTGGATCCGGCAGTTTCCAGGAAACAAACTGGAGTGGCTGGGCTACATAAGCT
TCAATGATAACACTAACTACAACCCATCTCTCAAAAGT**CGAATCTCTATCAC
TCGAGACACATCCAAGAACCAGTTCTTCCTGCAGTTGAATTCTGTGACTACTGA
GGACACAGC CACATATTACTGTACAAGGAGGGTGGACTACTGGGGTCAAGGA
ACCTCAGTCACCGTCTCCTCA

SEQ ID NO:4: GPR64-1 Light Chain Variable Region

GATGTTGTGATGACCCAAACTCCACTCTCCCTGCCTGTCAGTCTTGGAGATCAA
GCCTCCATCTCTTGC**AGATCTAGTCAGAGCCTTGTACACAGTAATGGAAACA
ACTATTTACAT**TGGTATTTGCAGAAGCCAGGCCAGTCTCCAAAGCTCCTGATCT
ACAAAGTTTCCAACCGATTTTCTGGGGTCCCAGACAGGTTCAGTGGCAGTGGA
TCAGGGACAGATTTCACACTCAAGATCAGCAGAGTGGAGGCTGAGGATCTGGG
AGTTTATTTCTGCTCTCAAAGTACACATGTTCCGTGGACGTTCGGTGGAGGCA
CCAAGCTGGAAATCAAA

SEQ ID NO:5: GPR64-16 Heavy Chain Variable Region

CAGGTTACTCTGAAAGAGTCTGGCCCTGGGATATTGCAGCCCTCCCAGACCCTC
AGTCTGACTTGTTCTTTCTCT**GGGTTTTCACTGAGCACTTCTGGTGTGGGTGT
GAGCTGGATTCGTCAGCCTTCAGGAAAGGGTCTGGAGTGGCTGGCACACATTT
ACTGGGATGATGATAAGCGCTATAACCCATCCCTGAAGAG**CCGGCTCACAA
TCTCCAAGGATACCTCCAGAAACCAGGTATTCCTCAAGATCACCAGTGTGGA CA
CTGCAGATACTGCCACATACTACTGTGCTCGA**AGAGTATTCATTATTACGGCC
TTTGACTAC**TGGGGCCAAGGCACCACTCTCACAGTCTCCTCA

<u>SEQ ID NO:6: GPR64-16 Light Chain Variable Region</u>
<u>GATATCCAGATGACACAGACTACATCCTCCCTGTCTGCCTCTCTGGGAGACAGA</u>
<u>GTCACCATCAGTTGCAGGGCAAGTCAGGACATTAGCAATTACTTAAAC</u>TGGT
ATCAGCAGAAACCAGATGGAACTGTTAAACTCCTGATCTACTACACATCAAACT
<u>TACACTCAGGAGTCCCATCA</u>AGGTTCAGTGGCAGTGGGTCTGGAGCAGATTAT
<u>TCTCTCACCATTGGCAACCTGGAGCAAGAAGATATTGCCACTTACTTTTGCCAA</u>
<u>CAGGGTAATACGCTTCCTTGGACG</u>TTCGGTGGAGGCACCAAGCTGGAAATCA
AA

FIG. 2

SEQ ID NO:7: GPR64-18 HEAVY CHAIN VARIABLE REGION
CAGGTTTCTCTGAAAGAGTCTGGCCCTGGGATATTGCAGCCCTCCCAGACCCTC
AGTCTGACTTGTTCTTTCTCT<u>GGGTTTTCACTGAGCACTTCTGGTATGGGTGTGA
GC</u>TGGATTCGTCAGCCTTCAGG AAAGGGTCTGGAGTGGCTGGCA <u>CACATTTACT
GGGATGATGACAAGCGCTATAACCCATCCCTGAAGAGC</u>CGGCTCACAATCTCC
AAGGATACCTCCAGCAACCTGGTATTCCTCAAGATCACC AGTGTGGACACTGCA
GATACTGCCACATACTACTG TGCTCGA<u>AGGGAAGTACGACGTGATTACTATGCT
ATGGACTAC</u>TGGGGTCAAGGAACCTCAGT CACCGTCTCCTCA

SEQ ID NO:8: GPR64-18 Light Chain Variable Region
AGTATTGTGATGACCCAGACTCCCAAATTCCTGCTTGTCTCAGCAGGAGACAGG
ATTACCATAGCCTGC<u>AGGGCCAGTCAGAGTGTGAGTAATGATGTAGCT</u>TGGT
ACCAACAGAAGCCAGGGCAGTCTCCTAAACTGCTGATAAAC<u>TATACATCCAAT
CGCTACACT</u>GGAGTCCCTGATCGCTTCACTGGCAGTGGATATGGGACGGATTT
CACTTTCACCATCAGCACTGTGCAGGCTGAAGACCTGGCAGTTTATTTCTGTCA
G<u>CAGGCTTATAGCTCTCCGTGGAC</u>GTTCGGTGGAGGCACCAAGCTGGAAATC
AAACGG

SEQ ID NO:9: GPR64-20 Heavy Chain Variable Region
GATGTGCAGCTTCAGGAGTCGGGACCTGGCCTGGTGAAACCTTCTCAGTCTCTG
TCCCTCACCTGCACTGTCACT<u>GGCTACTCAATCACCAGTGATTATGCCTGGAA
C</u>TGGATCCGGCAGTTTCCAGGAAACAAACTGGAGTGGATGGGC<u>TACATAAGCT
ACAGTGATTACACTAGCTACAACCCATCTCTCAAAAGT</u>CGAATCTCTATCAC
TCGAGACACATCCAAGAACCAGTTCTTCCTGCAGTTGAATTCTGTGACTACTGA
GGACACAGCCACATATTACTGTGCAAGA<u>AGGGTGGACTAC</u>TGGGGTCAAGGA
ACCTCAGTCACCGTCTCCTCA

SEQ ID NO:10: GPR64-20 Light Chain Variable Region
GATGTTGTGATGACCCAAACTCCACTCTCCCTGCCTGTCAGTCTTGGAGATCAA
GCCTCCATCTCTTGC<u>AGATCTAGTCAGAGCCTTGTACACAGTAATGGAAACA
CCTATTTACAT</u>TGGTACCTGCAGAAGCCAGGCCAGTCTCCAAAGCTCCTGATCT
AC<u>AAAGTTTCCAACCGATTTTCT</u>GGGGTCCCAGACAGGTTCAGTGGCAGTGGA
TCAGGGACAGATTTCACACTCAAGATCAGCAGAGTGGAGGCTGAGGATCTGGG
AGTTTATTTCTGC<u>TCTCAAAGTACACATGTTCCGTGGAC</u>GTTCGGTGGAGGCA
CCACGCTGGAAATCAAA

SEQ ID NO:11: GPR64-48 Heavy Chain Variable Region
GATGTGCAGCTTCAGGAGTCGGGACCTGGCCTGGTGAAACCTTCTCAGTCTCTG
TCCCTCACCTGCACTGTCACT<u>GGCTACTCAATCACCAGTGATTATGCCTGGAA
C</u>TGGATCCGGCAGTTTCCAGGAAACAAACTGGAGTGGATGGGC<u>TACATAAGCT
TCAGTGATAGCACTAGCTACAACCCATCTCTCAAAAGT</u>CGAATCTCTATCAC
TCGAGACACATCCAAGAACCAGTTCTTCCTGCAGTTGAATTCTGTGACTACTGA
GGACACAGCCACATATTACTGTGCAAGA<u>AGGGGGGACTAC</u>TGGGGTCAAGGA
ACCTCAGTCACCGTCTCCTCA

FIG. 2 (Con't.)

SEQ ID NO:12: GPR64-48 Light Chain Variable Region
GATGTTGTGATGACCCAAACTCCACTCTCCCTGCCTGTCAGTCTTGGAGATCAA
GCCTCCATCTCTTGC<u>AGATCTAGTCAGAGCCTTGTACACAGTAATGGAAACA
CCTATTTACAT</u>TGGTACCTGCAGAAGCCAGGCCAGTCTCCAAAGCTCCTGATCT
AC<u>AAAGTTTCCAACCGATTTTCT</u>GGGGTCCCAGACAGGTTCAGTGGCAGTGGA
TCAGGGACAGATTTCACACTCAAGATCAGCAGAGTGGAGGCTGAGGATCTGGG
AGTTTATTTCTGC<u>TCTCAAAGTACACATCTTCCG</u>TGGACGTTCGGTGGAGGCA
CCAAGCTGGAAATCAAA

AMINO ACID SEQUENCES

SEQ ID NO:13: GPR64-1 Heavy Chain Variable Region
DVQLQESGPGLVKPSQSLSLTCTVT <u>GYSITSDYAWN</u> WIRQFPGNKLEWLG <u>YISFND
NTNYNPSLKS</u> RISITRDTSKNQFFLQLNSVTTEDTATYYCTR <u>RVDY</u>WGQGTSVTVS
S

SEQ ID NO:14: GPR64-1 Light Chain Variable Region
DVVMTQTPLSLPVSLGDQASISC <u>RSSQSLVHSNGNNYLH</u> WYLQKPGQSPKLLIY<u>K
VSNRFS</u> GVPDRFSGSGSGTDFTLKISRVEAEDLGVYFC <u>SQSTHVPWT</u>FGGGTKLEI
K

SEQ ID NO:15: GPR64-16 Heavy Chain Variable Region
QVTLKESGPGILQPSQTLSLTCSFS<u>GFSLSTSGVGVS</u> WIRQPSGKGLEWLA <u>HIYWD
DDKRYNPSLKS</u> RLTISKDTSRNQVFLKITSVDTADTATYYCAR <u>RVFIITAFDY</u>WGQ
GTTLTVSS

SEQ ID NO:16: GPR64-16 Light Chain Variable Region
DIQMTQTTSSLSASLGDRVTISC<u>RASQDISNYLN</u>WYQQKPDGTVKLLIY<u>YTSNLHS</u>
GVPSRFSGSGSGADYSLTIGNLEQEDIATYFC<u>QQGNTLPWT</u>FGGGTKLEIK

SEQ ID NO:17: GPR64-18 Heavy Chain Variable Region
QVSLKESGPGILQPSQTLSLTCSFS<u>GFSLSTSGMGVS</u>WIRQPSGKGLEWLA <u>HIYWD
DDKRYNPSLKS</u> RLTISKDTSSNLVFLKITSVDTADTATYYCAR <u>REVRRDYYAMDY</u>
WGQGTSVTVSS

SEQ ID NO:18: GPR64-18 Light Chain Variable Region
SIVMTQTPKFLLVSAGDRITIAC<u>RASQSVSNDVA</u>WYQQKPGQSPKLLIN <u>YTSNRYT</u>
GVPD RFTGSGYGTDFTFTISTVQAEDLAVYFC<u>QQAYSSPWT</u>FGGGTKLEIK

FIG. 2 (Con't.)

SEQ ID NO :19: GPR64-20 Heavy Chain Variable Region
DVQLQESGPGLVKPSQSLSLTCTVT <u>GYSITSDYAWN</u> WIRQFPGNKLEWMG<u>YISYS
DYTSYNPSLKS</u> RISITRDTSKNQFFLQLNSVTTEDTATYYCAR<u>RVDY</u>WGQGTSVTV
SS

SEQ ID NO:20 GPR64-20 Light Chain Variable Region
DVVMTQTPLSLPVSLGDQASISC <u>RSSQSLVHSNGNTYLH</u> WYLQKPGQSPKLLIY<u>K
VSNRFS</u> GVPDRFSGSGSGTDFTLKISRVEAEDLGVYFC <u>SQSTHVPWT</u>FGGGTTLEIK

SEQ ID NO:21: GPR64-48 Heavy Chain Variable Region
DVQLQESGPGLVKPSQSLSLTCTVT <u>GYSITSDYAWN</u> WIRQFPGNKLEWMG<u>YISFSD
STSYNPSLKS</u> RISITRDTSKNQFFLQLNSVTTEDTATYYCAR <u>RGDY</u>WGQGTSVTVS
S

SEQ ID NO:22: GPR64-48 Light Chain Variable Region
DVVMTQTPLSLPVSLGDQASISC <u>RSSQSLVHSNGNTYLH</u> WYLQKPGQSPKLLIY<u>K
VSNRFS</u> GVPDRFSGSGSGTDFTLKISRVEAEDLGVYFC <u>SQSTHLPW</u>TFGGGTKLEIK

FIG. 2 (Con't.)

GPR+ Cells

| RNA+ | FACS expression | MTT effect |
|---|---|---|
| ME180 | + | + |
| H460 | + | + |
| H520 | + | + |
| C32 | + | - |
| DU145 | + | - |

GPR64- Cells

| RNA+ | FACS expression | MTT effect | RNA- | FACS expression | MTT effect |
|---|---|---|---|---|---|
| BT474 | - | - | HT1376 | ND | - |
| MCF7 | - | - | SW780 | - | + |
| NW231 | - | - | HCT116 | ND | - |
| H358 | - | - | SW620 | ND | - |
| Calu6 | - | - | U87 | - | - |
| SKOV3 | - | - | A549 | - | - |
| LnCAP | - | + | A375 | - | - |
| | | | C8161 | - | - |
| | | | ES2 | - | - |
| | | | OV-90 | ND | - |
| | | | OVCAR3 | - | - |
| | | | PA-1 | ND | - |
| | | | PC3 | - | - |

Fig. 4

| Mab | FACS (nM) | IHC | IF | Biacore | Isotype | | Mab | FACS (nM) | IHC | IF | Biacore | Isotype |
|---|---|---|---|---|---|---|---|---|---|---|---|---|
| 61a | 0.7288 | 3+ | 2+ | | | | 85a | 38.2 | 2+ | 2+ | 2.78E-09 | |
| 62a | 2.736 | 2+ | 2+ | 1.09E-09 | 2b | | 86a | 97.98 | neg | 1+ | | 2a |
| 65a | 1.371 | 2+ | 2+ | 1.73E-09 | 2b | | 87a | 77.04 | neg | - | | |
| 68a | 6.15 | 2+ | 1+ | 1.48E-09 | 2b | | 88a | 37.51 | neg | | | |
| 70a | 1.831 | 3+ | 2+ | | 1 | | 89a | 107 | 2+ | 2+ | | |
| 80a | 0.4032 | 2+ | 1+ | 1.22E-09 | 2b | | 90a | 194.6 | 3+ | 2+ | | 2a |
| 67a | 246.1 | 2+ | - | | 1 | | 91a | 4.252 | 2+ | 2+ | 8.01E-09 | |
| 69a | 295.6 | neg | - | | | | 93a | 1.269 | 2+ | 1+ | 1.66E-07 | |
| 71a | 8.159 | 2+ | - | | | | 94a | 87.84 | 3+ | 2+ | | 2b |
| 72a | 130.8 | neg | - | | 1 | | 95a | 28.81 | 2+ | 2+ | 6.29E-10 | 2a |
| 74a | 442.6 | 2+ | - | | | | 96a | 22.77 | 2+ | - | | |
| 75a | 102.4 | 2+ | 2+ | 9.68E-09 | | | 97a | | nd | | | |
| 76a | 0.8313 | 2+ | 2+ | 1.62E-10 | 2a | | 98a | 186.1 | nd | 2+ | 6.97E-09 | 1 |
| 77a | 0.9765 | 3+ | 1+ | 2.07E-09 | 1 | | 99a | 10.96 | 2+ | 2+ | 1.81E-09 | 2a |
| 78a | 8.955 | 2+ | 1+ | 4.06E-11 | 2a | | 100a | 42.1 | 2+ | 2+ | 1.46E-10 | 2a |
| 79a | 5.299 | 3+ | 1+ | | | | 101a | 4.939 | 3+ | - | | 1 |
| 81a | 0.0585 | 2+ | 1+ | 1.38E-08 | 1 | | 102a | 117.2 | nd | - | | 2a |
| 82a | 5.829 | 2+ | 2+ | 1.61E-09 | | | 103a | | nd | | | |
| 83a | 124.7 | 2+ | - | | | | 79b | | 3+ | | | |
| 84a | 113.6 | 2+ | - | | 2a | | 77b | | nd | | | |
| 18b1 | ~4.0 | 2+ | 1+ | 2.83E-09 | 1 | | 104 | | nd | | | |

Fig. 5

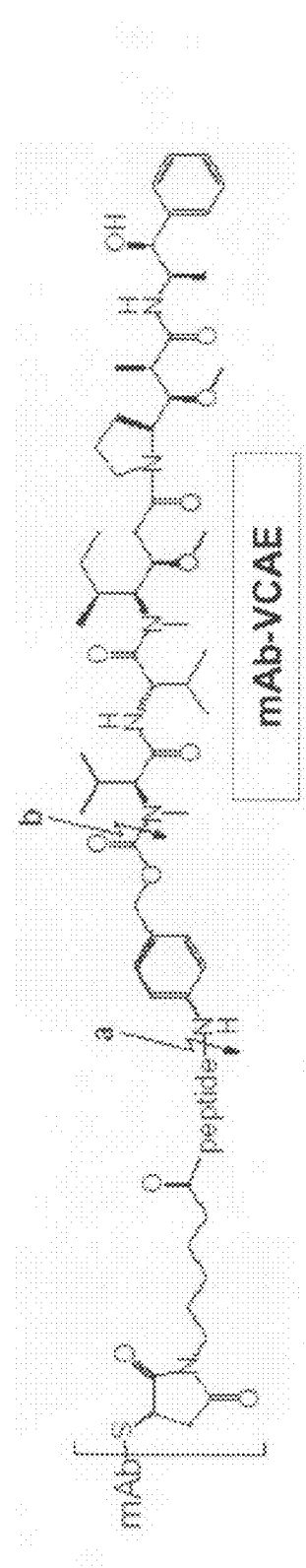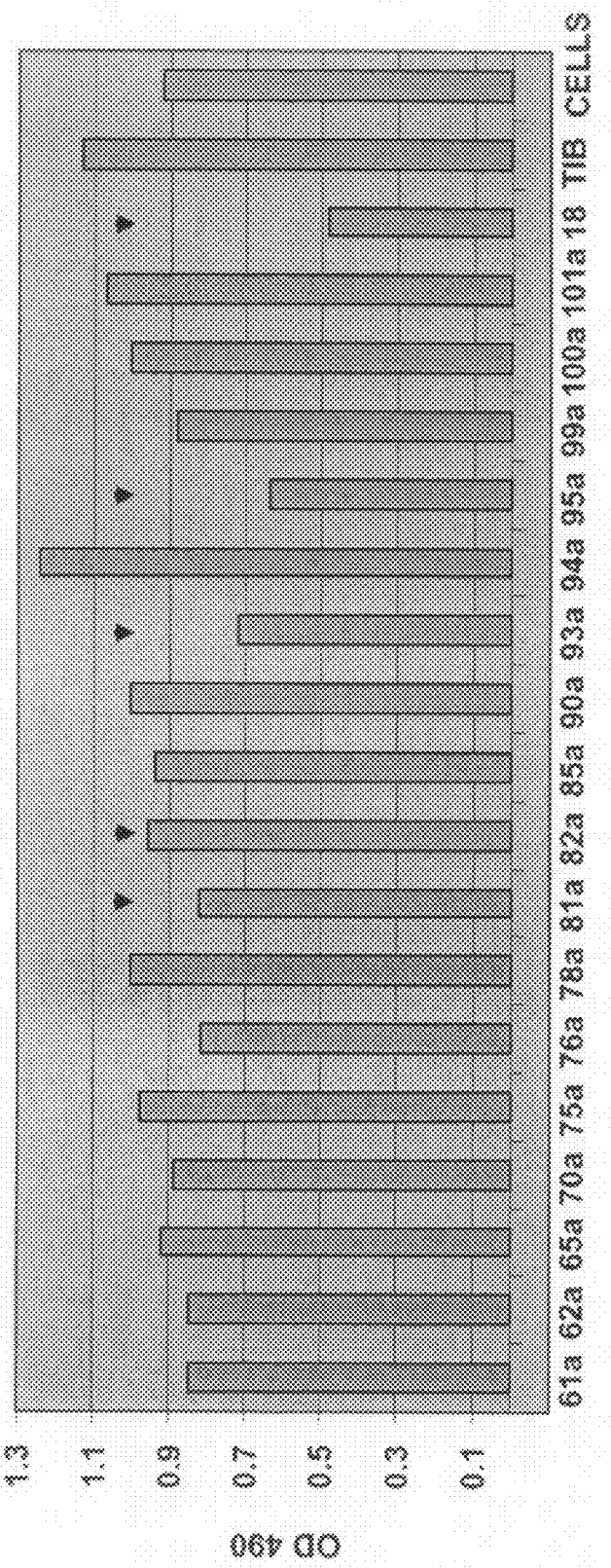
FIG. 9

ANTIBODIES AGAINST GPR64 AND USES THEREOF

RELATED APPLICATIONS

This application is a divisional of U.S. application Ser. No. 10/741,657 filed Dec. 19, 2003, which claims priority from U.S. Provisional Application No. 60/435,618 filed Dec. 20, 2002, which is hereby incorporated by reference in its entirety. This application is related to U.S. Ser. No. 60/350,666 filed Nov. 13, 2001, and U.S. Ser. No. 10/173,999, filed Jun. 17, 2002, each of which is hereby incorporated by reference in its entirety.

FIELD OF THE INVENTION

The invention relates to the identification and generation of antibodies that specifically bind to GPR64 proteins; and to the use of such antibodies and compositions comprising them in the diagnosis, prognosis and therapy of cancer.

BACKGROUND OF THE INVENTION

Ovarian cancer is the sixth most common cancer in women, accounting for 6% of all female cancers. It ranks fifth as the cause of cancer death in women. The American Cancer Society predicts that there will be about 23,100 new cases of ovarian cancer in this country in the year 2000 and about 14,000 women will die of the disease. Because many ovarian cancers cannot be detected early in their development, they account for a disproportionate number of fatal cancers, being responsible for almost half the deaths from cancer of the female genital tract; more deaths than any other reproductive organ cancer.

Most patients with epithelial ovarian cancer, the predominant form, are asymptomatic in early-stage disease and usually present with stage III or IV disease. Their five-year survival is less than 25%, with lower survival among African-American women. The minority of patients discovered with early-stage disease have a five-year survival rate of 80%-90% (Parker, S. L. et. al. Cancer statistics, 1997. CA 1997:47:5-27).

In the absence of a family history of ovarian cancer, lifetime risk of ovarian cancer is 1/70. Risk factors include familial cancer syndromes (risk of up to 82% by age 70 in women with hereditary breast/ovarian syndrome); family history (1.4% lifetime risk with no affected relatives, 5% with one affected relative, 7% with two affected relatives; Kerlikowske, K. et. al. Obstet Gynecol (1992) 80: 700-707) nulliparity; advancing age; obesity; personal history of breast, endometrial, or colorectal cancer; fewer pregnancies; or older age (>35 years) at first pregnancy. However, 95% of all ovarian cancers occur in women without risk factors. Use of hormonal contraceptives, oophorectomy, and tubal sterilization reduce risk of ovarian cancer (Kerlikowske, K. et. al. Obstet Gynecol (1992) 80: 700-707; Grimes, D. A. Am J. Obstet. Gynecol. (1992) 166: 1950-1954; Hankinson, S. E. et. al. (1993) JAMA 270: 2813-2818) however, even bilateral oophorectomy may not be completely effective in preventing ovarian cancer.

Treatment of ovarian cancer consists largely of surgical oophectemy, anti-hormone therapy, and/or chemotherapy. Although many ovarian cancer patients are effectively treated, the current therapies can all induce serious side effects which diminish quality of life. Deciding on a particular course of treatment is typically based on a variety of prognostic parameters and markers (Fitzgibbons et al., 2000, Arch. Pathol. Lab. Med. 124:966-978; Hamilton and Piccart, 2000, Ann. Oncol. 11:647-663), including genetic predisposition markers BRCA-1 and BRCA-2 (Robson, 2000, J. Clin. Oncol. 18:113-118).

The identification of novel therapeutic targets and diagnostic markers is essential for improving the current treatment of ovarian cancer patients. Recent advances in molecular medicine have increased the interest in tumor-specific cell surface antigens that could serve as targets for various immunotherapeutic or small molecule strategies. Antigens suitable for immunotherapeutic strategies should be highly expressed in cancer tissues and ideally not expressed in normal adult tissues. Expression in tissues that are dispensable for life, however, may be tolerated. Examples of such antigens include Her2/neu and the B-cell antigen CD20. Humanized monoclonal antibodies directed to Her2/neu (Herceptin®/trastuzumab) are currently in use for the treatment of metastatic breast cancer (Ross and Fletcher, 1998, Stem Cells 16:413-428). Similarly, anti-CD20 monoclonal antibodies (Rituxin®/rituximab) are used to effectively treat non-Hodgkin's lymphoma (Maloney et al., 1997, Blood 90:2188-2195; Leget and Czuczman, 1998, Curr. Opin. Oncol. 10:548-551).

Potential immunotherapeutic targets have been identified for ovarian cancer. One such target is polymorphic epithelial mucin (MUC1). MUC1 is a transmembrane protein, present at the apical surface of glandular epithelial cells. It is often overexpressed in ovarian cancer, and typically exhibits an altered glycosylation pattern, resulting in an antigenically distinct molecule, and is in early clinical trials as a vaccine target (Gilewski et al., 2000, Clin. Cancer Res. 6:1693-1701; Scholl et al., 2000, J. Immunother. 23:570-580). The tumor-expressed protein is often cleaved into the circulation, where it is detectable as the tumor marker, CA 15-3 (Bon et al., 1997, Clin. Chem. 43:585-593). However, many patients have tumors that express neither HER2 nor MUC-1; therefore, it is clear that other targets need to be identified to manage localized and metastatic disease.

While industry and academia have identified novel sequences, there has not been an equal effort exerted to identify the function of these novel sequences. The elucidation of a role for novel proteins and compounds in disease states for identification of therapeutic targets and diagnostic markers is essential for improving the current treatment of ovarian cancer patients. Accordingly, provided herein is a molecular target for therapeutic intervention in ovarian and other cancers. Additionally, provided herein are methods that can be used with this target in diagnosis and prognosis of ovarian cancer.

The GPR64 protein has been implicated in certain cancerous conditions, e.g. ovarian cancer, Ewing's sarcoma, and uterine cancer. Antibodies useful for diagnosis, prognosis, and effective treatment of cancer, including metastatic cancer, would be desirable. Accordingly, provided herein are compositions and methods that can be used in diagnosis, prognosis, and therapy of certain cancers.

GPR64 (also referred to in the literature as Ov1 and HE6, and sometimes referred to in this document and figures and OAM6) is an orphan G-protein coupled receptor with a large, heavily glycosylated N-terminal extracellular domain.

GPR64 has been cloned by Osterhoff et al., (1997, DNA AND CELL BIOLOGY 16:379-389) as an epididymus-specific G-protein coupled receptor (GPCR).

Gene expression profiling as described in U.S. Ser. No. 10/173,999, filed Jun. 17, 2002 (which is hereby incorporated by reference in its entirety), and the Examples contained herein, indicates that GPR64 is up-regulated in ovarian cancer tissue relative to normal tissue.

A bioinformatics analysis of the GPR64 gene sequence based on publicly available database information suggests that the protein product contains a signal sequence, a large extracellular domain (619 amino acids), seven transmembrane domains and is predicted to locate to the plasma membrane and function as a G-protein coupled receptor. This makes GPR64 an attractive target for therapeutic antibodies.

SUMMARY OF THE INVENTION

The present invention provides anti-GPR64 antibodies that are useful for making conjugated antibodies for therapeutic purposes. For example, the anti-GPR64 antibodies of the invention may be used as selective cytotoxic agents against GPR64 expressing tumor cells (e.g. ovarian cancer, uterine cancer and Ewing's sarcoma cells). In some embodiments, the antibodies of the present invention may be used therapeutically to treat patients suspected of having or those having been diagnosed with cancer and/or other proliferative conditions, including benign proliferative conditions. In one aspect, the GPR64 antibodies of the present invention are used to treat proliferative conditions of the ovary including, for example, ovarian cancer. In other embodiments, the antibodies may be used to treat uterine cancer, Ewing's sarcoma or any condition associated with GPR64 expressing cell proliferation.

The present invention provides high affinity antibodies for GPR64 protein (SEQ ID NO:2) encoded by the nucleotide sequence SEQ ID NO: 1. (Hs.421137, NM_005756.1). In one embodiment, the present invention provides an antibody that competitively inhibits binding of a GPR64 polypeptide to a GPR64 antibody selected from the group consisting GPR64-18, GPR64-81, GPR64-93, and GPR64-101. Other selected antibodies that may be useful in this embodiment are disclosed in FIG. 5. In some embodiments, the invention provides an antibody conjugated to an effector moiety or component. The effector moiety may be a label (e.g., a fluorescent label, an effector domain, e.g. MicA) or can be a cytotoxic agent (e.g., a radioisotope or a cytotoxic chemical). In one preferred embodiment, the antibody of the present invention cytotoxic agent auristatin. In other embodiments the antibodies may be used alone to inhibit tumor cell growth. In another preferred embodiment of the invention, the antibody mediates antibody dependent cellular toxicity.

The GPR64 antibodies provided by the present invention include chimeric, humanized and human antibodies. In some embodiments, the invention provides primatized GPR64 antibodies for treatment of primate patients. The present invention provides GPR64 antibodies that are whole antibodies, as well as GPR64 antibody fragments. In preferred embodiments the antibody fragments include Fab, Fab', F(ab')$_2$, Fv fragments, rIgG, diabodies, single chain antibodies, and multispecific antibodies.

Antibodies of the present invention include antibodies with 95% or greater homology to the nucleotide and amino acid sequences of the V$_H$ and V$_L$ regions disclosed in FIG. 2 (SEQ ID NOs: 3-22). In one preferred embodiment, the invention provides an antibody comprising SEQ ID NO:17 and/or SEQ ID NO:18, which correspond to the V$_H$ and V$_L$ regions of GPR64-18, respectively.

The present invention also provides a monoclonal antibody (or antibody fragment thereof) that binds a polypeptide that comprises a sequence at least 80% homologous (and preferably 98% homologous) to the sequence from amino acid 1 to and including amino acid 588 of GPR64 (SEQ ID NO:2). In some embodiments, the GPR64 monoclonal antibody of the invention is chimeric, humanized or human. Preferably, the monoclonal antibody competes for a ligand binding site on GPR64, and more preferably it inhibits proliferation of tumor cells in vivo, wherein the tumor cells are selected from the group consisting of ovarian cancer, Ewing's sarcoma, uterine cancer, and other GPR64-expression tumor cells. In some embodiments, the monoclonal antibody is conjugated to an effector moiety, such as a cytotoxic agent (e.g. auristatin). In an additional embodiment, the invention provides a monoclonal antibody that mediates antibody dependent cellular cytotoxicity.

In another embodiment, the invention provides monoclonal antibody that binds to the same GPR64 epitope as that bound by an antibody selected from group consisting of GPR64-18, GPR64-81, GPR64-93, and GPR64-101.

The invention also provides a monoclonal antibody, wherein the antibody binds to the same GPR64 epitope as that bound by the monoclonal antibody produced by a hybridoma cell line binds selected from the group consisting of: ATCC accession number PTA-5703 (hybridoma OAM6#81); and ATCC accession number PTA-5704 (hybridoma OAM6#93).

In another embodiment, the invention provides the host cells capable of producing any of the GPR64 antibody embodiments. In preferred embodiments, the host cell is selected from the group consisting of a Chinese Hamster Ovary (CHO) cell, *E. coli*, yeast cell, and insect cell.

In another embodiment, the invention provides the hybridomas capable of producing any of the GPR64 monoclonal antibody embodiments. In one preferred embodiment, the invention provides a hybridoma selected from the group consisting of hybridoma cell lines: ATCC accession number PTA-5703 (hybridoma OAM6#81); and ATCC accession number PTA-5704 (hybridoma OAM6#93).

The invention also provides pharmaceutical compositions comprising a pharmaceutically acceptable excipient and any of the GPR64 antibody embodiments of the invention. In some embodiments of the pharmaceutical composition, the GPR64 antibody is conjugated to an effector moiety or component. The effector component may be a label (e.g., a fluorescent label) or can be cytotoxic agent (e.g., a radioisotope or a cytotoxic chemical moiety). The invention provides a variety of cytoxic agents that may be conjugated to a GPR64 antibody including: diphtheria A chain, exotoxin A chain, ricin A chain, abrin A chain, curcin, crotin, phenomycin, neomycin and auristatin. In one preferred embodiment, the cytotoxic agent is auristatin. The antibodies in the pharmaceutical compositions may be whole antibodies or may be antibody fragments (e.g. include Fab, Fab', F(ab')$_2$, Fv fragments, rIgG, diabodies, single chain antibodies, and multispecific antibodies). In some embodiments, the pharmaceutical composition includes a chimeric, humanized, or human GPR64 antibody.

In one alternative embodiment, the invention provides a composition comprising an antibody and a pharmaceutically acceptable carrier or excipient, wherein the antibody is a monoclonal antibody produced by a hybridoma cell line selected from the group consisting of ATCC accession number PTA-5703 (hybridoma OAM6#81); and ATCC accession number PTA-5704 (hybridoma OAM6#93).

The invention also provides methods of inhibiting proliferation of an ovarian cancer-associated cell. The method comprises contacting the cell with a GPR64 antibody of the invention. In most embodiments, the cancer cell is in a patient, typically a human. The patient may be diagnosed with and undergoing a therapeutic regimen to treat a metastatic ovarian cancer, or may simply be suspected of having ovarian cancer.

The present invention also provides methods of treatment using GPR64 and the associated composition embodiments. For example, the invention provides a method of inhibiting the growth of tumor cells comprising: administering to a mammal (preferably a human) a therapeutically effective amount of an antibody capable of binding to an amino acid sequence having at least 80% homology to a sequence from amino acid 1 to and including amino acid 588 of SEQ ID NO:2. In preferred embodiments, the antibody of the method is conjugated to an effector moiety (e.g. auristatin), or the antibody mediates antibody dependent cellular cytotoxicity. In preferred embodiments, the method inhibits the growth of tumor cells comprising a carcinoma selected from the group consisting of ovarian cancer, Ewing's sarcoma, uterine cancer, and other GPR64 expressing tumor cell types.

In alternative embodiments of the method comprising administering an antibody and a therapeutically effective amount of a cytotoxic agent to a patient, the antibodies and cytotoxic agent may administered simultaneously, or either one before the other. In another alternative, the cytotoxic agent is conjugated to the antibody and thereby added simultaneously.

The invention further provides diagnostic tests and immunoassays employing the various GPR64 antibody embodiments. In preferred embodiments, these methods involve detecting a cancer cell in a biological sample from a patient by contacting the biological sample with an antibody of the invention. In some embodiments, the antibody is conjugated to a label such as fluorescent label or radioisotope.

In one preferred embodiment, the invention provides a method of diagnosing a tumor in a mammal, comprising: contacting an antibody with a test sample obtained from the mammal; and detecting the formation of a complex between the antibody and a polypeptide of the test sample; wherein the antibody binds the polypeptide comprising an amino acid sequence having at least 80% homology to the sequence from amino acid 1 to and including amino acid 588 of SEQ ID NO:2. In preferred embodiments of this method, the test sample is obtained from an individual suspected of having neoplastic cell growth or proliferation, or from an individual suspected of having ovarian cancer.

In an alternative embodiment, the invention provides a method of producing high serum titers of specific antibodies to cell surface receptor proteins comprising: providing a cell surface receptor with a mutation that uncouples the receptor from it signaling system; transfecting and expressing the mutant receptor in a cell line; and passively immunizing a mammal with the cell line; whereby specific antibodies to the cell surface receptor are produced in high serum titer. In a preferred embodiment, this method may be carried out wherein the cell surface receptor is a G protein coupled receptor, preferably GPR64. In other preferred embodiments, the mutation of the method is a DRY box mutation and the cell line used with the method is the Balb/c syngeneic cell line 3T12.

BRIEF DESCRIPTION OF THE DRAWINGS

FIG. 1 depicts the nucleotide and amino acid sequences of GPR64 (SEQ ID NOs: 1 and 2)

FIG. 2 depicts the nucleotide and amino acid sequences of $V_H$ and $V_L$ regions of the five anti-GPR64 antibodies: GPR64-1, -16, -18, -20 and -48. (SEQ ID NOs: 3-22)

FIG. 4 depicts list data showing that GPR64 expression down-modulation by RNAi in cell proliferation in GPR64 expressing cancer cells.

FIG. 5 depicts a table summarizing results of binding studies on a panel of 42 anti-GPR64 monoclonal antibodies.

FIG. 9 depicts a schematic of the mAb-auristatin (mAb-VCAE) conjugate and a plot of H460 4-day growth in the presence of various GPR64 mAb-VCAE conjugates.

DETAILED DESCRIPTION OF THE INVENTION

Figure 3:
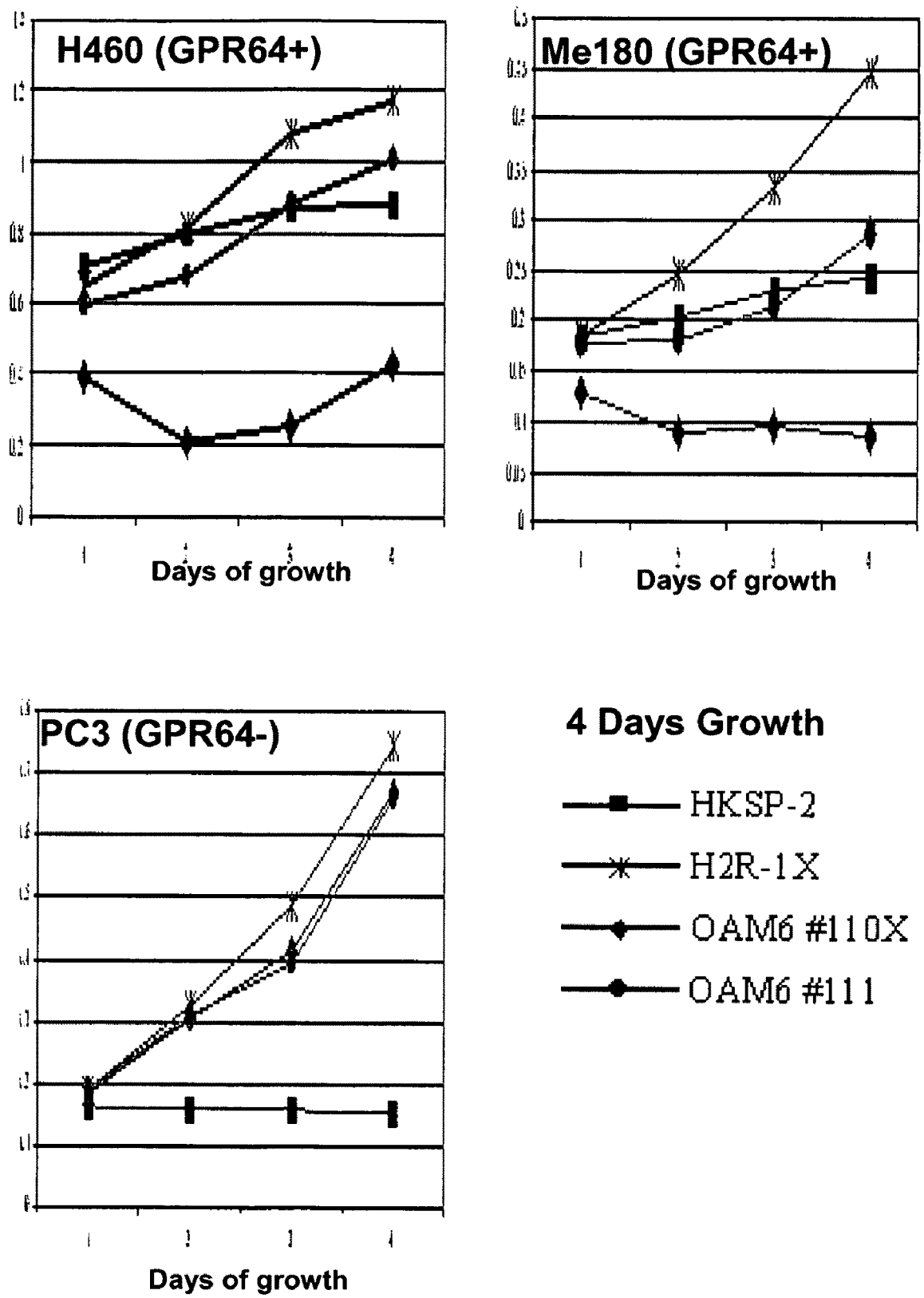
FIG. 3 depicts plots of 4-day growth assay data showing that GPR64 expression down-modulation by RNAi in cell proliferation in GPR64 expressing cancer cells.

The present invention provides novel reagents and methods for treatment, diagnosis and prognosis for certain cancers using antibodies against GPR64. In particular, the present invention provides anti-GPR64 antibodies that are particularly useful as selective cytotoxic agents for GPR64 expressing cells.

Epitope mapping of antibodies showing high affinity binding can be carried out through competitive binding analyses well-known in the art and described further below. Using this methodology, antibodies recognizing a number of individual epitopes can be identified. The antibodies are then assessed for GPR64 dependent cell death in vitro. Using these methods antibodies that promote significant cell death can be identified

DEFINITIONS

As used herein, "antibody" includes reference to an immunoglobulin molecule immunologically reactive with a particular antigen, and includes both polyclonal and monoclonal antibodies. The term also includes genetically engineered forms such as chimeric antibodies (e.g. humanized murine antibodies) and heteroconjugate antibodies (e.g., bispecific antibodies). The term "antibody" also includes antigen binding forms of antibodies, including fragments with antigen-binding capability (e.g., Fab', F(ab')$_2$, Fab, Fv and rIgG. See also, Pierce Catalog and Handbook, 1994-1995 (Pierce Chemical Co., Rockford, Ill.). See also, e.g., Kuby, J., Immunology, 3$^{rd}$ Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) J Immunol 148:1547, Pack and Pluckthun (1992) Biochemistry 31:1579, Hollinger et al., 1993, supra, Gruber et al. (1994) J Immunol: 5368, Zhu et al. (1997) Protein Sci 6:781, Hu et al. (1996) Cancer Res. 56:3055, Adams et al. (1993) Cancer Res. 53:4026, and McCartney, et al. (1995) Protein Eng. 8:301.

An antibody immunologically reactive with a particular antigen can be generated by recombinant methods such as selection of libraries of recombinant antibodies in phage or similar vectors, see, e.g., Huse et al., Science 246:1275-1281 (1989); Ward et al., Nature 341:544-546 (1989); and Vaughan et al., *Nature Biotech.* 14:309-314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs". The extent of the framework regions and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "$V_H$" refer to the variable region of an immunoglobulin heavy chain of an antibody, including the heavy chain of an Fv, scFv, or Fab. References to "$V_L$" or a "$V_L$" refer to the variable region of an immunoglobulin light chain, including the light chain of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

An antibody having a constant region substantially identical to a naturally occurring class IgG antibody constant region refers to an antibody in which any constant region present is substantially identical, i.e., at least about 85-90%, and preferably at least 95% identical, to the amino acid sequence of the naturally occurring class IgG antibody's constant region.

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies useful with the present invention may be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow and Lane, "Antibodies: A Laboratory Manual," Cold Spring Harbor Laboratory Press, New York (1988); Hammerling et al., in: "Monoclonal Antibodies and T-Cell Hybridomas," Elsevier, N.Y. (1981), pp. 563-681 (both of which are incorporated herein by reference in their entireties).

In many preferred uses of the present invention, including in vivo use of the GPR64 antibodies in humans for and in vitro detection assays, it may be preferable to use chimeric, primatized, humanized, or human antibodies.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. Methods for producing chimeric antibodies are known in the art. See e.g., Morrison, Science 229:1202-1207 (1985); Oi et al., BioTechniques 4:214-221 (1986); Gillies et al., J. Immunol. Methods 125:191-202 (1989); U.S. Pat. Nos. 5,807,715; 4,816,567; and 4,816,397, which are incorporated herein by reference in their entireties.

The term "humanized antibody" or "humanized immunoglobulin" refers to an immunoglobulin comprising a human framework, at least one and preferably all complementarity determining regions (CDRs) from a non-human antibody, and in which any constant region present is substantially identical to a human immunoglobulin constant region, i.e., at least about 85-90%, and preferably at least 95% identical. Hence, all parts of a humanized immunoglobulin, except possibly the CDRs, are substantially identical to corresponding parts of one or more native human immunoglobulin sequences. Accordingly, such humanized antibodies are chimeric antibodies (U.S. Pat. No. 4,816,567), wherein substantially less than an intact human variable domain has been substituted by the corresponding sequence from a non-human species. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. Nos. 5,530,101; 5,585,089; 5,693,761; 5,693,762; 6,180,370 (each of which is incorporated by reference in its entirety). Antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592,106; EP 519,596; Padlan, Mol. Immunol., 28:489-498 (1991); Studnicka et al., Prot. Eng. 7:805-814 (1994); Roguska et al., Proc. Natl. Acad. Sci. 91:969-973 (1994), and chain shuffling (U.S. Pat. No. 5,565,332), all of which are hereby incorporated by reference in their entireties.

Completely "human" antibodies may be desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins, but which can express human immunoglobulin genes. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633, 425; 5,569,825; 5,661,016; 5,545,806; 5,814,318; 5,885,793; 5,916,771; and 5,939,598, which are incorporated by reference herein in their entireties. In addition, companies such as Abgenix, Inc. (Fremont, Calif.) and Medarex (Princeton, N.J.) can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., Biotechnology 12:899-903 (1988).

The term "primatized antibody" refers to an antibody comprising monkey variable regions and human constant regions. Methods for producing primatized antibodies are known in the art. See e.g., U.S. Pat. Nos. 5,658,570; 5,681,722; and 5,693,780, which are incorporated herein by reference in their entireties.

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

Antibodies of "IgG class" refers to antibodies of IgG1, IgG2, IgG3, and IgG4. The numbering of the amino acid residues in the heavy and light chains is that of the EU index (Kabat, et al., "Sequences of Proteins of Immunological Interest", $5^{th}$ ed., National Institutes of Health, Bethesda, Md. (1991); the EU numbering scheme is used herein).

The term "GPR64" refers to nucleic acid and polypeptide polymorphic variants, alleles, mutants, and interspecies homologues that: (1) have a nucleotide sequence that has greater than about 60% nucleotide sequence identity, 65%, 70%, 75%, 80%, 85%, 90%, or more preferably 91%, 92%, 93%, 94%, 95%, 96%, 97%, 98% or 99% or greater nucleotide sequence identity, preferably over a region of at least about 25, 50, 100, 200, 500, 1000, or more nucleotides, to a nucleotide sequence of SEQ ID NO: 1; (2) bind to antibodies, e.g., polyclonal antibodies, raised against an immunogen comprising an amino acid sequence encoded by a nucleotide sequence of SEQ ID NO: 1, and conservatively modified variants thereof, (3) specifically hybridize under stringent hybridization conditions to a nucleic acid sequence, or the complement thereof of SEQ ID NO: 1 and conservatively modified variants thereof or (4) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino sequence identity, preferably over a region of at least about 25, 50, 100, 200, or more amino acids, to an amino acid sequence of SEQ ID NO:2. A polynucleotide or polypeptide sequence is typically from a mammal including, but not limited to, primate, e.g., human; rodent, e.g., rat, mouse, hamster; cow, pig, horse, sheep, or other mammal. A "GPR64 polypeptide" and a "GPR64 polynucleotide," include both naturally occurring or recombinant forms.

A "full length" GPR64 protein or nucleic acid refers to a ovarian cancer polypeptide or polynucleotide sequence, or a variant thereof, that contains all of the elements normally contained in one or more naturally occurring, wild type GPR64 polynucleotide or polypeptide sequences. For example, a full length GPR64 nucleic acid will typically comprise all of the exons that encode for the full length, naturally occurring protein. The "full length" may be prior to, or after, various stages of post-translation processing or splicing, including alternative splicing.

"Biological sample" as used herein is a sample of biological tissue or fluid that contains nucleic acids or polypeptides, e.g., of a GPR64 protein, polynucleotide or transcript. Such samples include, but are not limited to, tissue isolated from primates (e.g., humans), or from rodents (e.g., mice, and rats). Biological samples may also include sections of tissues such as biopsy and autopsy samples, frozen sections taken for histologic purposes, blood, plasma, serum, sputum, stool, tears, mucus, hair, skin, etc. Biological samples also include explants and primary and/or transformed cell cultures derived from patient tissues. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

"Providing a biological sample" means to obtain a biological sample for use in methods described in this invention. Most often, this will be done by removing a sample of cells from an animal, but can also be accomplished by using previously isolated cells (e.g., isolated by another person, at another time, and/or for another purpose), or by performing the methods of the invention in vivo. Archival tissues, having treatment or outcome history, will be particularly useful.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., Nuc. Acids Res. 25:3389-3402 (1977) and Altschul et al., J. Mol. Biol. 215:403-410 (1990). BLAST and BLAST 2.0 are used, with the parameters described herein, to determine percent sequence identity for the nucleic acids and proteins of the invention. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be large negative numbers, e.g., 5, 10, 20, 30, 40, 40, 70, 90, 110, 150, 170, etc.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as E. coli, or eukaryotic cells such as yeast, insect, amphibian, or mammalian cells such as CHO, HeLa, and the like (see, e.g., the American Type Culture Collection catalog or web site, www.atcc.org).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG, and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Macromolecular structures such as polypeptide structures can be described in terms of various levels of organization. For a general discussion of this organization, see, e.g., Alberts et al., *Molecular Biology of the Cell* (3rd ed., 1994) and Cantor & Schimmel, Biophysical Chemistry Part J: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that often form a compact unit of the polypeptide and are typically 25 to approximately 500 amino acids long. Typical domains are made up of sections of lesser organization such as stretches of (-sheet and (-helices. "Tertiary structure" refers to the complete three dimensional structure of a polypeptide monomer. "Quaternary structure" refers to the three dimensional structure formed, usually by the noncovalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include fluorescent dyes, electron-dense reagents, enzymes (e.g., as commonly used in an ELISA), biotin, digoxigenin, colloidal gold, luminescent nanocrystals (e.g. quantum dots), haptens and proteins or other entities which can be made detectable, e.g., by incorporating a radiolabel into the peptide or used to detect antibodies specifically reactive with the peptide. The radioisotope may be, for example, $^3$H, $^{14}$C, $^{32}$P, $^{35}$S, or $^{125}$I. In some cases, particularly using antibodies against the proteins of the invention, the radioisotopes are used as toxic moieties, as described below. The labels may be incorporated into the GPR64 nucleic acids, proteins and antibodies at any position. Any method known in the art for conjugating the antibody to the label may be employed, including those methods described by Hunter et al., *Nature*, 144:945 (1962); David et al., Biochemistry, 13:1014 (1974); Pain et al., *J. Immunol. Meth.*, 40:219 (1981); and Nygren, *J. Histochem. and Cytochem.*, 30:407 (1982). The lifetime of radiolabeled peptides or radiolabeled antibody compositions may extended by the addition of substances that stabilize the radiolabeled peptide or antibody and protect it from degradation. Any substance or combination of substances that stabilize the radiolabeled peptide or antibody may be used including those substances disclosed in U.S. Pat. No. 5,961,955.

An "effector" or "effector moiety" or "effector component" is a molecule that is bound (or linked, or conjugated), either covalently, through a linker or a chemical bond, or noncovalently, through ionic, van der Waals, electrostatic, or hydrogen bonds, to an antibody. The "effector" can be a variety of molecules including, e.g., detection moieties including radioactive compounds, fluorescent compounds, an enzyme or substrate, tags such as epitope tags, a toxin, activatable moieties, a chemotherapeutic or cytotoxic agent, a chemoattractant, a lipase; an antibiotic; or a radioisotope emitting "hard" e.g., beta radiation.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g., paclitaxel (TAXOL®, Bristol-Myers Squibb Oncology, Princeton, N.J.), and doxetaxel (TAXOTERE®, Rhone-Poulenc Rorer, Antony, Rnace), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, caminomycin, aminopterin, dactinomycin, mitomycins, esperamicins (see U.S. Pat. No. 4,675, 187), 5-FU, 6-thioguanine, 6-mercaptopurine, actinomycin D, VP-16, chlorambucil, melphalan, and other related nitrogen mustards. Also included in this definition are hormonal agents that act to regulate or inhibit hormone action on tumors such as tamoxifen and onapristone.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids, antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming, counterions such as sodium; and/or nonionic surfactants such as TWEEN™, polyethylene glycol (PEG), and PLURONICS™.

A "therapeutically effective amount", in reference to the treatment of tumor, refers to an amount capable of invoking one or more of the following effects: (1) inhibition, to some extent, of tumor growth, including, slowing down and complete growth arrest; (2) reduction in the number of tumor cells; (3) reduction in tumor size; (4) inhibition (i.e., reduction, slowing down or complete stopping) of tumor cell infiltration into peripheral organs; (5) inhibition (i.e., reduction, slowing down or complete stopping) of metastasis; (6) enhancement of anti-tumor immune response, which may, but does not have to, result in the regression or rejection of the tumor; and/or (7) relief, to some extent, of one or more symptoms associated with the disorder. A "therapeutically effective amount" of a GPR64 antibody for purposes of treatment of tumor may be determined empirically and in a routine manner.

"Treatment" refers to both therapeutic treatment and prophylactic or preventative measures. Those in need of treatment include those already with the disorder as well as those in which the disorder is to be prevented.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, e.g., through the expression of a recombinant nucleic acid as depicted above.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background.

Specific binding to an antibody under such conditions requires an antibody that is selected for its specificity for a particular protein. For example, polyclonal antibodies raised to a particular protein, polymorphic variants, alleles, orthologs, and conservatively modified variants, or splice variants, or portions thereof, can be selected to obtain only those polyclonal antibodies that are specifically immunoreactive with GPR64 and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include highest cancer, prostate cancer, colon cancer, squamous cell cancer, small-cell lunge cancer, non-small cell lunar cancer, gastrointestinal cancer, pancreatic cancer, glioblastoma cervical cancer, ovarian cancer, liver cancer, bladder cancer, hepatoma, colorectal cancer, endometrial carcinoma, salivary gland carcinoma kidney cancer, liver cancer, vulval cancer, thyroid cancer, hepatic carcinoma and various types of head and neck cancer.

"Tumor", as used herein, refers to all neoplastic cell growth and proliferation, whether malignant or benign, and all pre-cancerous and cancerous cells and tissues.

Expression of GPR64 Polypeptides from Nucleic Acids

Nucleic acids of the invention can be used to make a variety of expression vectors to express GPR64 polypeptides which can then be used to raise antibodies of the invention, as described below. Expression vectors and recombinant DNA technology are well known to those of skill in the art and are used to express proteins. The expression vectors may be either self-replicating extrachromosomal vectors or vectors which integrate into a host genome. Generally, these expression vectors include transcriptional and translational regulatory nucleic acid operably linked to the nucleic acid encoding the GPR64 protein. The term "control sequences" refers to DNA sequences used for the expression of an operably linked coding sequence in a particular host organism. Control sequences that are suitable for prokaryotes, e.g., include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is typically accomplished by ligation at convenient restriction sites. If such sites do not exist, synthetic oligonucleotide adaptors or linkers are used in accordance with conventional practice. Transcriptional and translational regulatory nucleic acid will generally be appropriate to the host cell used to express the GPR64 protein. Numerous types of appropriate expression vectors, and suitable regulatory sequences are known in the art for a variety of host cells.

In general, transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, an expression vector may comprise additional elements. For example, the expression vector may have two replication systems, thus allowing it to be maintained in two organisms, e.g. in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art (e.g., Fernandez & Hoeffler, supra).

In addition, in a preferred embodiment, the expression vector contains a selectable marker gene to allow the selection of transformed host cells. Selection genes are well known in the art and will vary with the host cell used.

The GPR64 proteins of the present invention are produced by culturing a host cell transformed with an expression vector containing nucleic acid encoding a GPR64 protein, under the appropriate conditions to induce or cause expression of the GPR64 protein. Conditions appropriate for GPR64 protein expression will vary with the choice of the expression vector and the host cell, and will be easily ascertained by one skilled in the art through routine experimentation or optimization. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Saccharomyces cerevisiae* and other yeasts, *E. coli, Bacillus subtilis*, Sf9 cells, C129 cells, 293 cells, Neurospora, BHK, CHO, COS, HeLa cells, HUVEC (human umbilical vein endothelial cells), THP1 cells (a macrophage cell line) and various other human cells and cell lines.

In a preferred embodiment, the GPR64 proteins are expressed in mammalian cells. Mammalian expression systems are also known in the art, and include retroviral and adenoviral systems. One expression vector system is a retroviral vector system such as is generally described in PCT/US97/01019 and PCT/US97/01048, both of which are hereby expressly incorporated by reference. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter (see, e.g., Fernandez & Hoeffler, supra). Typically, transcription termination and polyadenylation sequences recognized by mammalian cells are regulatory regions located 3' to the translation stop codon and thus, together with the promoter elements, flank the coding sequence. Examples of transcription terminator and polyadenlyation signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In some embodiments, GPR64 proteins are expressed in bacterial systems. Bacterial expression systems are well known in the art. Promoters from bacteriophage may also be used and are known in the art. In addition, synthetic promoters and hybrid promoters are also useful; e.g., the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the GPR64 protein in bacteria. The protein is either secreted into the growth media (gram-positive bacteria) or into the periplasmic space, located between the inner and outer membrane of the cell (gram-negative bacteria). The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors. Expression vectors for bacteria are well known in the art, and include vectors for *Bacillus subtilis, E. coli, Streptococcus cremoris*, and *Streptococcus lividans*, among others. The bacterial expression vectors are transformed into bacterial host cells using techniques well known in the art, such as calcium chloride treatment, electroporation, and others.

In one embodiment, GPR64 polypeptides are produced in insect cells. Expression vectors for the transformation of insect cells, and in particular, baculovirus-based expression vectors, are well known in the art.

GPR64 polypeptides can also be produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*.

The GPR64 polypeptides may also be made as a fusion protein, using techniques well known in the art. Thus, e.g., for the creation of monoclonal antibodies, if the desired epitope is small, the GPR64 protein may be fused to a carrier protein to form an immunogen. Alternatively, the GPR64 protein may be made as a fusion protein to increase expression, or for other reasons. For example, when the GPR64 protein is a GPR64 peptide, the nucleic acid encoding the peptide may be linked to other nucleic acid for expression purposes.

The GPR64 polypeptides are typically purified or isolated after expression. GPR64 proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the GPR64 protein may be purified using a standard anti-GPR64 protein antibody column. Ultrafiltration and diafiltration techniques, in conjunction with protein concentration, are also useful. For general guidance in suitable purification techniques, see Scopes, Protein Purification (1982).

The degree of purification necessary will vary depending on the use of the GPR64 protein. In some instances no purification will be necessary.

One of skill will recognize that the expressed protein need not have the wild-type GPR64 sequence but may be derivative or variant as compared to the wild-type sequence. These variants typically fall into one or more of three classes: substitutional, insertional or deletional variants. These variants ordinarily are prepared by site specific mutagenesis of nucleotides in the DNA encoding the protein, using cassette or PCR mutagenesis or other techniques well known in the art, to produce DNA encoding the variant, and thereafter expressing the DNA in recombinant cell culture as outlined above. However, variant protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the GPR64 protein amino acid sequence. The variants typically exhibit the same qualitative biological activity as the naturally occurring analogue, although variants can also be selected which have modified characteristics as will be more fully outlined below.

GPR64 polypeptides of the present invention may also be modified in a way to form chimeric molecules comprising a GPR64 polypeptide fused to another, heterologous polypeptide or amino acid sequence. In one embodiment, such a chimeric molecule comprises a fusion of the GPR64 polypeptide with a tag polypeptide which provides an epitope to which an anti-tag antibody can selectively bind. The epitope tag is generally placed at the amino- or carboxyl-terminus of the GPR64 polypeptide. The presence of such epitope-tagged forms of a GPR64 polypeptide can be detected using an antibody against the tag polypeptide. Also, provision of the epitope tag enables the GPR64 polypeptide to be readily purified by affinity purification using an anti-tag antibody or another type of affinity matrix that binds to the epitope tag. In an alternative embodiment, the chimeric molecule may comprise a fusion of a GPR64 polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; HIS6 and metal chelation tags, the flu HA tag polypeptide and its antibody 12CA5 (Field et al., *Mol. Cell. Biol.* 8:2159-2165 (1988)); the c-myc tag and the 8F9, 3C7, 6E10, G4, B7 and 9E10 antibodies thereto (Evan et al., *Molecular and Cellular Biology* 5:3610-3616 (1985)); and the Herpes Simplex virus glycoprotein D (gD) tag and its antibody (Paborsky et al., Protein Engineering 3(6):547-553 (1990)). Other tag polypeptides include the FLAG-peptide (Hopp et al., *BioTechnology* 6:1204-1210 (1988)); the KT3 epitope peptide (Martin et al., *Science* 255:192-194 (1992)); tubulin epitope peptide (Skinner et al., *J. Biol. Chem.* 266:15163-15166 (1991)); and the T7 gene 10 protein peptide tag (Lutz-Freyermuth et al., *Proc. Natl. Acad. Sci. USA* 87:6393-6397 (1990)).

Antibodies to GPR64 Polypeptides

Once the GPR64 protein is produced, it is used to generate antibodies, e.g. for immunotherapy or immunodiagnosis. In some embodiments of the invention, the antibodies recognize the same epitope as the CDRs shown in Table 2. The ability of a particular antibody to recognize the same epitope as another antibody is typically determined by the ability of one antibody to competitively inhibit binding of the second antibody to the antigen. Any of a number of competitive binding assays can be used to measure competition between two antibodies to the same antigen. An exemplary assay is a Biacore® assay as described in the Examples, below. Briefly in these assays, binding sites can be mapped in structural terms by testing the ability of interactants, e.g. different antibodies, to inhibit the binding of another. Injecting two consecutive antibody samples in sufficient concentration can identify pairs of competing antibodies for the same binding epitope. The antibody samples should have the potential to reach a significant saturation with each injection. The net binding of the second antibody injection is indicative for binding epitope analysis. Two response levels can be used to describe the boundaries of perfect competition versus non-competing binding due to distinct epitopes. The relative amount of binding response of the second antibody injection relative to the binding of identical and distinct binding epitopes determines the degree of epitope overlap.

Other conventional immunoassays known in the art can be used in the present invention. For example, antibodies can be differentiated by the epitope to which they bind using a sandwich ELISA assay. This is carried out by using a capture antibody to coat the surface of a well. A subsaturating concentration of tagged-antigen is then added to the capture surface. This protein will be bound to the antibody through a specific antibody:epitope interaction. After washing a second antibody, which has been covalently linked to a detectable moeity (e.g., HRP, with the labeled antibody being defined as the detection antibody) is added to the ELISA. If this antibody recognizes the same epitope as the capture antibody it will be unable to bind to the target protein as that particular epitope will no longer be available for binding. If however this second antibody recognizes a different epitope on the target protein it will be able to bind and this binding can be detected by quantifying the level of activity (and hence antibody bound) using a relevant substrate. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pair-wise manner to determine epitope specificity.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays described above.

Methods of preparing polyclonal antibodies are known to the skilled artisan (e.g., Coligan, supra; and Harlow & Lane, supra). Polyclonal antibodies can be raised in a mammal, e.g., by one or more injections of an immunizing agent and, if desired, an adjuvant. Typically, the immunizing agent and/or adjuvant will be injected in the mammal by multiple subcutaneous or intraperitoneal injections. The immunizing agent may include a protein encoded by a nucleic acid of the figures or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler & Milstein, *Nature* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a polypeptide encoded by nucleic acid of SEQ ID NO: 1 or a fragment thereof, or a fusion of protein sequence of SEQ ID NO:2 or fragments thereof.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, pp. 59-103 (1986)). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

FIG. 2 depicts the nucleotide and amino acid sequences of the $V_H$ and $V_L$ regions of five GPR64 monoclonal antibodies: GPR64-1, -16, -18, -20 and -48. (SEQ ID NOs: 3-22). In addition, 41 more mAbs generated from a GPR64-Fc fusion in accordance with standard methods are listed in a table in FIG. 5 along with their binding properties. Two of these GPR64 mAbs, #81 and #93 (also referred to as OAM6#81 and OAM6#93), were deposited at the ATCC on Dec. 19, 2003.

In some embodiments the antibodies to the GPR64 proteins are chimeric or humanized antibodies. As noted above, humanized forms of antibodies are chimeric immunoglobulins in which residues from a complementary determining region (CDR) of human antibody are replaced by residues from a CDR of a non-human species such as mouse, rat or rabbit having the desired specificity, affinity and capacity.

Human antibodies can be produced using various techniques known in the art, including phage display libraries (Hoogenboom & Winter, *J. Mol. Biol.* 227:381 (1991); Marks et al., *J. Mol. Biol.* 222:581 (1991)). The techniques of Cole et al. and Boerner et al. are also available for the preparation of human monoclonal antibodies (Cole et al., *Monoclonal Antibodies and Cancer Therapy*, p. 77 (1985) and Boerner et al., *J. Immunol.* 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633, 425; 5,661,016, and in the following scientific publications: Marks et al., *Bio/Technology* 10:779-783 (1992); Lonberg et al., *Nature* 368:856-859 (1994); Morrison, *Nature* 368:812-

13 (1994); Fishwild et al., Nature Biotechnology 14:845-51 (1996); Neuberger, *Nature Biotechnology* 14:826 (1996); Lonberg & Huszar, *Intern. Rev. Immunol.* 13:65-93 (1995).

In some embodiments, the antibody is a single chain Fv (scFv). The $V_H$ and the $V_L$ regions of a scFv antibody comprise a single chain which is folded to create an antigen binding site similar to that found in two chain antibodies. Once folded, noncovalent interactions stabilize the single chain antibody. While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g. Huston et al., *Proc. Nat'l Acad. Sci. USA* 8:5879 (1988); Bird et al., *Science* 242:4236 (1988); Glockshuber et al., *Biochemistry* 29:1362 (1990); U.S. Pat. No. 4,946,778, U.S. Pat. No. 5,132,405 and Stemmer et al., *Biotechniques* 14:256-265 (1993). Generally the peptide linker will have no specific biological activity other than to join the regions or to preserve some minimum distance or other spatial relationship between the $V_H$ and $V_L$. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of the sequence Gly-Gly-Gly-Gly-Ser, preferably 2, 3, 4, 5, or 6 such sequences. However, it is to be appreciated that some amino acid substitutions within the linker can be made. For example, a valine can be substituted for a glycine.

Methods of making scFv antibodies have been described. See, Huse et al., supra; Ward et al. supra; and Vaughan et al., supra. In brief, mRNA from B-cells from an immunized animal is isolated and cDNA is prepared. The cDNA is amplified using primers specific for the variable regions of heavy and light chains of immunoglobulins. The PCR products are purified and the nucleic acid sequences are joined. If a linker peptide is desired, nucleic acid sequences that encode the peptide are inserted between the heavy and light chain nucleic acid sequences. The nucleic acid which encodes the scFv is inserted into a vector and expressed in the appropriate host cell. The scFv that specifically bind to the desired antigen are typically found by panning of a phage display library. Panning can be performed by any of several methods. Panning can conveniently be performed using cells expressing the desired antigen on their surface or using a solid surface coated with the desired antigen. Conveniently, the surface can be a magnetic bead. The unbound phage are washed off the solid surface and the bound phage are eluted.

Finding the antibody with the highest affinity is dictated by the efficiency of the selection process and depends on the number of clones that can be screened and the stringency with which it is done. Typically, higher stringency corresponds to more selective panning. If the conditions are too stringent, however, the phage will not bind. After one round of panning, the phage that bind to GPR64 coated plates or to cells expressing GPR64 on their surface are expanded in *E. coli* and subjected to another round of panning. In this way, an enrichment of many fold occurs in 3 rounds of panning. Thus, even when enrichment in each round is low, multiple rounds of panning will lead to the isolation of rare phage and the genetic material contained within which encodes the scFv with the highest affinity or one which is better expressed on phage.

Regardless of the method of panning chosen, the physical link between genotype and phenotype provided by phage display makes it possible to test every member of a cDNA library for binding to antigen, even with large libraries of clones.

In one embodiment, the antibodies are bispecific antibodies. Bispecific antibodies are monoclonal, preferably human or humanized, antibodies that have binding specificities for at least two different antigens or that have binding specificities for two epitopes on the same antigen. In one embodiment, one of the binding specificities is for the GPR64 protein, the other one is for another cancer antigen. Alternatively, tetramer-type technology may create multivalent reagents.

In some embodiments, the antibodies to GPR64 protein are capable of reducing or eliminating cells expressing GPR64 (e.g. ovarian cancer cells). Generally, at least a 25% decrease in activity, growth, size or the like is preferred, with at least about 50% being particularly preferred and about a 95-100% decrease being especially preferred.

By immunotherapy is meant treatment of ovarian cancer with an antibody raised against GPR64 proteins. As used herein, immunotherapy can be passive or active. Passive immunotherapy as defined herein is the passive transfer of antibody to a recipient (patient). Active immunization is the induction of antibody and/or T-cell responses in a recipient (patient). Induction of an immune response is the result of providing the recipient with an antigen (e.g., GPR64 or DNA encoding it) to which antibodies are raised. As appreciated by one of ordinary skill in the art, the antigen may be provided by injecting a polypeptide against which antibodies are desired to be raised into a recipient, or contacting the recipient with a nucleic acid capable of expressing the antigen and under conditions for expression of the antigen, leading to an immune response.

In some embodiments, the antibody is conjugated to an effector moiety. The effector moiety can be any number of molecules, including labeling moieties such as radioactive labels or fluorescent labels, or can be a therapeutic moiety. In one aspect the therapeutic moiety is a small molecule that modulates the activity of the GPR64 protein. In another aspect the therapeutic moiety modulates the activity of molecules associated with or in close proximity to the GPR64 protein.

In other embodiments, the therapeutic moiety is a cytotoxic agent. In this method, targeting the cytotoxic agent to ovarian cancer tissue or cells, results in a reduction in the number of afflicted cells, thereby reducing symptoms associated with ovarian cancer. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin, auristatin and the like. Cytotoxic agents also include radiochemicals made by conjugating radioisotopes to antibodies raised against ovarian cancer proteins, or binding of a radionuclide to a chelating agent that has been covalently attached to the antibody. Targeting the therapeutic moiety to transmembrane ovarian cancer proteins not only serves to increase the local concentration of therapeutic moiety in the ovarian cancer afflicted area, but also serves to reduce deleterious side effects that may be associated with the therapeutic moiety.

Binding Affinity of Antibodies of the Invention

The antibodies of the invention specifically bind to GPR64 polypeptides. In preferred embodiments, the antibodies bind to GPR64 with very high affinity and exhibit $K_D$ values of less the 1 µM, preferably less than about 0.01 µM, and most preferably, 0.01 µM, or even subnanomolar.

In one embodiment, affinity of a GPR64 antibody may be determined by assaying competitive inhibition versus another GPR64 antibody (e.g. one of known affinity) for binding to a GPR64 polypeptide. Strong competitive inhibition indicates a strong binding affinity for GPR64.

Binding affinity for a target antigen is typically measured or determined by standard antibody-antigen assays, such as Biacore® competitive assays, saturation assays, or immunoassays such as ELISA or RIA.

Such assays can be used to determine the dissociation constant of the antibody. The phrase "dissociation constant" refers to the affinity of an antibody for an antigen. Specificity of binding between an antibody and an antigen exists if the dissociation constant ($K_D$=1/K, where K is the affinity constant) of the antibody is <1 µM, preferably <100 nM, and most preferably <0.1 nM. Antibody molecules will typically have a $K_D$ in the lower ranges. $K_D$=[Ab–Ag]/[Ab] [Ag] where [Ab] is the concentration at equilibrium of the antibody, [Ag] is the concentration at equilibrium of the antigen and [Ab–Ag] is the concentration at equilibrium of the antibody-antigen complex. Typically, the binding interactions between antigen and antibody include reversible noncovalent associations such as electrostatic attraction, Van der Waals forces and hydrogen bonds.

Immunoassays

The antibodies of the invention can be used to detect GPR64 or GPR64 expressing cells using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37, Asai, ed. Academic Press, Inc. New York (1993); *Basic and Clinical Immunology* 7th Edition, Stites & Terr, eds. (1991).

Thus, the present invention provides methods of detecting cells that express GPR64. In one method, a biopsy is performed on the subject and the collected tissue is tested in vitro. The tissue or cells from the tissue is then contacted with an anti-GPR64 antibody of the invention. Any immune complexes which result indicate the presence of a GPR64 protein in the biopsied sample. To facilitate such detection, the antibody can be radiolabeled or coupled to an effector moiety which is a detectable label, such as a radio label.

In another method, the cells may be detected in vivo using typical imaging systems. Then, the localization of the label is determined by any of the known methods for detecting the label. A conventional method for visualizing diagnostic imaging can be used. For example, paramagnetic isotopes can be used for MRI. Internalization of the antibody may be important to extend the life within the organism beyond that provided by extracellular binding, which will be susceptible to clearance by the extracellular enzymatic environment coupled with circulatory clearance.

GPR64 proteins can also be detected using standard immunoassay methods and the antibodies of the invention. Standard methods include, for example, radioimmunoassay, sandwich immunoassays (including ELISA), immunofluorescence assays, Western blot, affinity chromatography (affinity ligand bound to a solid phase), and in situ detection with labeled antibodies.

Suppression of Endogenous GPR64 Gene Expression Through the Use of RNAi

In many species, introduction of double-stranded RNA (dsRNA) which may alternatively be referred to herein as small interfering RNA (siRNA), induces potent and specific gene silencing, a phenomena called RNA interference or RNAi. This phenomenon has been extensively documented in the nematode *C. elegans* (Fire, A., et al, Nature, 391, 806-811, 1998), but is widespread in other organisms, ranging from trypanasomes to mouse. Depending on the organism being discussed, RNA interference has been referred to as "cosuppression", "post-transcriptional gene silencing", "sense suppression" and "quelling".

RNAi is an attractive as a biotechnological tool because it provides a means for knocking out the activity of specific genes. It is particularly useful for knocking out gene expression in species that were not previously considered to be amenable to genetic analysis or manipulation.

In designing RNAi experiments there are several factors that need to be considered such as the nature of the dsRNA, the durability of the silencing effect, and the choice of delivery system.

To produce an RNAi effect, the dsRNA, or siRNA that is introduced into the organism should contain exonic sequences. Furthermore, the RNAi process is homology dependent, so the sequences must be carefully selected so as to maximize gene specificity, while minimizing the possibility of cross-interference between homologous, but not gene-specific sequences. Preferably the dsRNA exhibits greater than 90% or even 100% identity between the sequence of the dsRNA and the gene to be inhibited. Sequences less than about 80% identical to the target gene are substantially less effective. Thus, the greater homology between the dsRNA and the gene whose expression is to be inhibited, the less likely expression of unrelated genes will be affected.

In addition, the size of the dsRNA is important. Often dsRNA greater than 500 base pairs in length is used, however, smaller fragments can also produce an RNAi effect.

Introduction of dsRNA into can be achieved by any methods known in the art, including for example, microinjection or electroporation. A variety of mechanisms by which dsRNA may inhibit gene expression have been proposed, but evidence in support of any specific mechanism is lacking (Fire, A., 1999).

Administration of Pharmaceutical and Vaccine Compositions

The antibodies of the invention may be formulated in pharmaceutical compositions. Thus, the present invention also provides methods and compositions for administering a therapeutically effective dose of an anti-GPR64 antibody. The exact dose will depend on the purpose of the treatment, and will be ascertainable by one skilled in the art using well-known techniques (e.g., Ansel et al., *Pharmaceutical Dosage Forms and Drug Delivery*; Lieberman, Pharmaceutical Dosage Forms (vols. 1-3, 1992), Dekker, ISBN 0824770846, 082476918X, 0824712692, 0824716981; Lloyd, *The Art, Science and Technology of Pharmaceutical Compounding* (1999); and Pickar, *Dosage Calculations* (1999)). As is known in the art, adjustments for ovarian cancer degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art. U.S. patent application Ser. No. 09/687,576, further discloses the use of compositions and methods of diagnosis and treatment in ovarian cancer is hereby expressly incorporated by reference.

A "patient" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human.

The administration of the antibodies of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly.

The pharmaceutical compositions of the present invention comprise an antibody of the invention in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody of the invention dissolved in a pharmaceutically acceptable carrier or excipient, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., *Remington's Pharmaceutical Science* (15th ed., 1980) and Goodman & Gillman, *The Pharmacologial Basis of Therapeutics* (Hardman et al., eds., 1996)).

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art, e.g., *Remington's Pharmaceutical Science* and Goodman and Gillman, *The Pharmacological Basis of Therapeutics*, supra.

The compositions containing antibodies of the invention can be administered for therapeutic or prophylactic treatments. In therapeutic applications, compositions are administered to a patient suffering from a disease (e.g., a cancer) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient. An amount of modulator that is capable of preventing or slowing the development of cancer in a mammal is referred to as a "prophylactically effective dose." The particular dose required for a prophylactic treatment will depend upon the medical condition and history of the mammal, the particular cancer being prevented, as well as other factors such as age, weight, gender, administration route, efficiency, etc. Such prophylactic treatments may be used, e.g., in a mammal who has previously had cancer to prevent a recurrence of the cancer, or in a mammal who is suspected of having a significant likelihood of developing cancer.

It will be appreciated that the present ovarian cancer protein-modulating compounds can be administered alone or in combination with additional ovarian cancer modulating compounds or with other therapeutic agent, e.g., other anti-cancer agents or treatments.

Kits for Use in Diagnostic and/or Prognostic Applications

For use in diagnostic, research, and therapeutic applications suggested above, kits are also provided by the invention. In the diagnostic and research applications such kits may include any or all of the following: assay reagents, buffers, and GPR64-specific antibodies of the invention. A therapeutic product may include sterile saline or another pharmaceutically acceptable emulsion and suspension base.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like.

Such media may include addresses to internet sites that provide such instructional materials.

EXAMPLES

Example 1

GPR64 Gene Expression Profiling in Ovarian Cancer and Normal Tissues

This example describes the use of GeneChip expression profiling to identify GPR64 as a valid ovarian cancer target.

Summary

Gene expression of 66 ovarian cancer samples was compared to 347 normal adult tissues representing 58 different organs. The goal was to look for genes that are up-regulated in ovarian cancer and are localized to the cell surface for antibody accessibility, but have little to no expression in vital organs to minimize undesirable side effects of a therapeutic antibody. Genes with the desired expression profile were examined by extensive bioinformatic analysis to determine their structural and functional classification, and determine their potential for cell surface localization. The GPR64 gene (National Center for Biotechnology Information reference sequence no. NM-005756.1; Ref Osterhoff et al., 1997, DNA Cell Biol. 16:379-389) displayed all the desired characteristics.

RNA Extraction and Microarray Protocols.

Preparation of Total RNA from Fresh-Frozen Prostate and Xenograft Tissue was performed by extraction with TRI-ZOL® reagent (Life Technologies, Inc., Gaithersburg, Md.) and was reverse transcribed using a primer containing oligodeoxythymidylic acid and a T7 promoter sequence. The resulting cDNAs were then in vitro transcribed in the presence of biotinylated nucleotides (Bio-11-CTP and Bio-16-UTP) using the T7 MEGASCRIPT® kit (Ambion, Austin, Tex.).

The biotinylated targets were hybridized to the Eos Hu03, a customized Affymetrix® GENECHIP® (Affymetrix, Santa Clara, Calif.) oligonucleotide array comprising 59,619 probesets representing 46,000 unique sequences including both known and FGENESH predicted exons that were based on the first draft of the human genome. The Hu03 probesets consist of perfect match probes only, most probesets having 6 or 7 probes. Hybridization signals were visualized using phycoerythrin-conjugated streptavidin (Molecular Probes, Eugene, Oreg.).

Normalization of the gene expression data was performed as follows. The probe-level intensity data from each array were fitted to a fixed distribution, using an inverse function to map the empirical cumulative distribution of intensities to the desired distribution. This procedure is akin to other per-chip normalization procedures, such as fixing the mean and SD of each chip to a standard value, except it is more stringent in that it fixes the entire distribution rather than one or two parameters. The purpose of per-chip normalization is to remove between-chip variation, on the assumption that it is attributable to nonbiological factors, i.e., technical noise. The scale parameter for the distribution was chosen to yield a distribution with an arbitrary mean value of 300, and the shape parameter of 0.81 was chosen to reproduce the typical shape of the empirical distribution seen in good samples.

A single measure of average intensity was calculated for each probeset using Tukey's trimean of the intensity of the constituent probes (Tukey J. W. Exploratory Data Analysis, Addison-Wesley Reading, Mass. 1977). The trimean is a measure of central tendency that is resistant to the effects of outliers. Finally, a background subtraction was applied to each average intensity measure to correct for nonspecific hybridization. The average intensity measure of a "null" probeset consisting of 491 probes with scrambled sequence was subtracted from all of the other probesets on the chip.

Results

GPR64 was significantly over expressed in ovarian cancer compared to normal body tissues. Some expression was detected in normal dorsal-root ganglia and parathyroid glands. No expression was detected in normal ovary as well as the rest of the normal tissues tested. Among non-ovarian cancer tissues, high expression levels were also detected in Ewing sarcoma. Lower levels of GPR64 expression were detected in uterine cancers, but no expression was seen in other cancers including colon, breast, prostate, lung, pancreatic and kidney cancers.

Example 2

Anti-GPR64 Inhibits Tumor Cell Growth In Vivo

The following example illustrates that GPR64 antibodies are effective at reducing tumor volume in vivo.

Animal studies were conducted using SCID mice immunized with the Human tumor cell line NC1-H460. The NC1-H460 cell line expresses the antigen recognized by antibody GPR64-18. The $V_H$ and $V_L$ nucleotide and amino acid sequences of antibody GPR64-18 are provided in FIG. 2 (SEQ ID NOs:7, 8, 17, 18).

The antibodies were made via standard methods using a fusion protein between the large N-terminus of GPR64 and human Fc as the immunogen.

To initiate tumor growth in vivo SCID mice were injected with the NC1-H460 tumor cell line and tumors were allowed to grow. When tumors reach a size of between 50-100 mm$^3$, animals were distributed into groups and subjected to treatment with either:

a.) an isotype control antibody;
b.) one of the five GPR64 antibodies, whose $V_H$ and $V_L$ sequences depicted in FIG. 2 (SEQ ID NOs:2-22), or
c.) one of the five GPR64 antibodies in conjunction with the chemotherapeutic agents, paclitaxel and carboplatin.

Antibodies were administered every 2 days at a dose of 10 mg/kg. For the antibody plus chemotherapy group, chemotherapies were administered together at 4 day intervals for 4 doses and the antibodies were administered at 10 mg/kg at 4 day intervals for 3 doses. Tumor size was measure twice weekly for 20 days.

The results of these experiments showed that in comparison with mice receiving treatment with the isotype control antibody, the mice receiving treatment with GPR64-18 antibody experienced a significant reduction in tumor volume.

Experiments that compared tumor reduction effected by antibodies in combination with chemotherapy showed that tumor volume was reduced to a greater extent when the GPR64 antibody was used in combination with the chemotherapy than when the isotype control antibody was combined with the chemotherapeutic agent. Furthermore, GPR64-18 antibodies had an additive effect in combination with the chemotherapeutic agent.

Thus, GPR64-18 antibodies are effective at reducing tumor volume and may be used to provide effective treatment for cancers where the GPR64 protein is expressed. In addition, any antibodies that bind GPR64 protein in such a way as to inhibit the binding of GPR64-18 antibody, may also be used to provide effective treatment for cancers where GPR64 protein is expressed.

Furthermore, since the effects of GPR64 antibodies and chemotherapeutic agents on tumor volume reduction are additive, the use of GPR64 antibodies will reduce the amount of chemotherapeutic agent necessary for effective reduction of tumor size in cancer patients, thereby reducing patient suffering due to toxic side effects of chemotherapeutic agents.

Example 3

GPR64 Knockdown by RNAi inhibits Cell Proliferation of GPR64 Expressing Cancer Cells The following example illustrates that GPR64 expression is essential for tumor cell growth in vitro and validates GPR64 as an ovarian cancer target.

Proteins can be down-regulated using short interfering double stranded RNAs (siRNA) specific to the cognate mRNA of the protein of interest. This approach was used to show that inhibition of GPR64 down-regulates cell growth and causes cell death. Thus, these experiments are consistent with the results of the experiments described in Example 2 and thereby confirm the basic conclusion that down-regulation of GPR64 expression will provide an effective treatment for cancers involving GPR64 protein expression.

RNAi Assay Method

Plasmids encoding an siRNA specific for GPR64, or a control siRNA, were introduced into two GPR64+ human tumor cell lines that require GPR64 for growth: H460, MeI 80. In addition, the same siRNAs were introduced into GPR64−, PC3 cells that do not require GPR64 for growth. The level of GPR64 protein was followed using FACS, and the effect on growth were assessed using an assay that measures cell survival and proliferation.

Human tumor cells were transfected with OAM6 siRNAs using Lipofectamine-2000 (Invitrogen) as follows: Lipofectamine-2000 was diluted in 1:50 in Minimal Essential Medium without phenol red (Invitrogen) and mixed in equal volumes with the appropriate siRNA at 120 nM in MEM. The Lipofectamine-2000/siRNA mixture was placed into a 96 well plate, and cells were pipetted on top, for a final siRNA concentration of 10 nM. Transfected cells were incubated at 37C; the extent of cell proliferation was determined 24, 48, 72, and 96 hours post-transfection with an MTS assay using the CellTiter 96® AQueous Non-Radioactive Cell Proliferation Assay (Promega Corporation), according to the manufacturer's instructions. Absorbance was read at 490 nm. Each data point represents the average of triplicate wells.

siRNAs were purchased from Dharmacon as duplexes with 3'dTdT overhangs. The following siRNA sequences used were:

```
H2R-1 (negative control) sense:
                                    (SEQ ID NO: 23)
5'-CAGACACGGCCACGUGUGAdTdT-3'

H2R-1 antisense:
                                    (SEQ ID NO: 24)
5'-UCACACGUGGCCGUGUCUGdTdT-3'

HKSP-1 (positive control) sense:
                                    (SEQ ID NO: 25)
5'-GCUAGCGCCCAUUCAAUAGdTdT-3'

HKSP-1 antisense:
                                    (SEQ ID NO: 26)
5'-CUAUUGAAUGGGCGCUAGCdTdT-3'

OAM6-110 sense:
                                    (SEQ ID NO: 27)
5'-GCUUACUCCCUUCAAACGAdTdT-3'

OAM6-110 antisense:
                                    (SEQ ID NO: 28)
5'-UCGUUUGAAGGGAGUAAGCdTdT-3'

OAM6-111 sense:
                                    (SEQ ID NO: 29)
5'-CCCCAGAGAAAUAUCUGCAdTdT-3'

OAM6-111 antisense:
                                    (SEQ ID NO: 30)
5'-UGCAGAUAUUUCUCUGGGGdTdT-3'
```

Results

The siRNA OAM6-110 caused significantly greater down-modulation of GPR64 protein expression than OAM6-111, as measured by FACS assay. Furthermore, those cells that exhibited down-regulation of GPR64 protein expression, experienced a dramatic decrease in cell proliferation. As shown in FIG. 3, while both siRNAs OAM6-110 and OAM6-111 caused a detectable effect on cell proliferation, the decreased cell proliferation observed with OAM6-110 was much greater than observed with OAM6-111 in both of the GPR64 positive cell lines (H460 and MeI 80). This relative difference in decreased cell growth between OAM6-110 and OAM6-111 correlated with the relative difference in GPR64 protein down-modulation observed for these two siRNAs via the FACS assay.

Interestingly, the effect of OAM6-110 was even stronger than that of a positive control siRNA, kinesin (HKSP-1) in H460 and MeI80 cells. Furthermore, HKSP-1 essentially abolishes cell proliferation in PC3, which does not express GPR64, and is not affected by either siRNA OAM6-110 or 111 indicating specificity.

The siRNA analysis was expanded to a larger panel of GPR64 positive and negative cell lines. As shown in FIG. 4, three out of five GPR+ cell lines showed proliferation effects when challenged with GPR64 siRNA. In contrast, only two, of 22 GPR64− cell lines were found to show marginal proliferation effects when treated with the GPR64 siRNA. These results strongly correlate GPR64 expression with susceptibility to GPR64 siRNA.

These siRNA results strongly supports the conclusion that GPR64 is required for the proliferation of endogenous GPR64 expressing cell lines and ovarian tumors, therefore validating GPR64 as a functional target for ovarian cancer.

Example 4

Panel of Monoclonal Antibodies to GPR64

A panel of monoclonal antibodies was generated and screened for high binding affinity to GPR64 using standard techniques.

Mice were immunized with a GPR64-Fc fusion protein. The fusion construct linked amino acids 1-588 of the full-length GPR64 sequence (SEQ ID NO:2) to an Fc protein. Spleen cells were fused and the original hybridomas were screened initially by FACS and ELISA, and later for proliferation effects, IHC on frozen tissue sections, and for off-rate binding kinetics. Approximately 40 clones were selected for subcloning based on tight binding and low off-rate. The subclones were expanded and purified. The purified monoclonal antibodies were then compared with one another by FACS titration, immunofluorescence and Biacore® and assessed for in vitro and vivo effects on proliferation.

FACS Assay

Cells were removed with 5 mM EDTA in Tris-HCl (pH 8.0) and blocked by centrifugation in HBSS containing 3% heat-inactivated FBS, 1% normal goat serum (Sigma), and 1% BSA at 4° C. for 5 min. Cells were incubated for 1 h at 4° C. with anti-GPR64-FITC (10 µg/ml; R&D Systems) in FACS buffer (PBS containing 0.1% BSA). Excess mAb was removed by centrifugation, and cells were resuspended in FACS buffer containing propidium iodide (1 µg/ml). Fluorescence intensity was measured on a FACScan (Becton Dickinson). Quantitative FACS was performed in a similar manner, except that a saturating concentration of anti-GPR64-FITC (50 µg/ml) was used on cells and similarly treated Quantum Simply Cellular™ beads (Sigma), a mixture of four populations of agarose beads of known antibody binding content. Antibody binding site quantification was performed by comparing the MFI of each cell line with that of the Quantum Simply Cellular™ bead populations and were corrected for nonspecific effects as described (Brockhoff et al., 1994, Cytometry 17: 75-83). Experiments were performed twice in triplicate.

Kinetic Analysis by Surface Plasmon Resonance

Kinetics measurements between human GPR64-Fc fusion protein and GPR64 monoclonal antibodies were performed using BIAcore 3000 (BIAcore, Sweden). Anti-GPR64 mAbs were immobilized with 100 RUs on Research-grade CM5 sensor chip by the BIAcore amine coupling reagents (N-ethyl-N'-dimethylaminopropylcarbodiimide, EDC; N-hydroxysuccinimide, NHS; and ethanolamine HCl, pH8.5). Assays were run at a flow rate of 30 ul/min at room temperature. Three-minute association phase of each GPR64-Fc was followed by ten-minute injection of running buffer (10 mM Hepes, 300 mM sodium chloride, 3 mM EDTA, 0.05% P-20, pH7.4) to monitor dissociation. The mAb surface was regenerated with 25 mM NaOH. The binding kinetics of each GPR64-mAb pair was calculated from the data at six different concentrations (2048 nM, 512 nM, 128 nM, 32 nM, 8 nM, 2 nM) of GPR64-Fc analyte, using the BIAevaluate program. Double referencing was applied in each analysis to eliminate background responses from reference surface and buffer only control. The affinity ($K_D$) of binding was obtained by simultaneously fitting the association and dissociation phases of the sensorgram from the analyte concentration series using the bivalent analyte model from BIAevaluate software.

Immunofluorescence and Internalization Assay

Cells grown on coverslips were chilled on ice in growth medium for 10 min. Growth medium was replaced with medium containing anti-GPR64 mAb (10 µg/ml) at 4° C. for 1 h. Antibody binding was detected using ALEXAFLUOR®-488 goat anti-mouse secondary antibody (1:2200 dilution in chilled growth media; Molecular Probes). Cells were washed three times with PBS, fixed using 5% UltraPure Formaldehyde in PBS for 40 min and washed two additional times using PBS. Slides were mounted using Permafluor™ (Coulter) for visualization.

In order to assay internalization of GPR64 antibodies, cells were placed in an incubator at 37° C. for 1 h and then placed on ice for 1 h in blocking solution (20 ug/ml pure Goat anti-mouse antibody in media). After washing in PBS, cells were fixed in 5% ultra pure formaldehyde. Cells were then washed with 0.5% Triton X-1000 and incubated with AlexaFluor-488 goat anti-mouse secondary antibody (1:2200 dilution in chilled growth media; Molecular Probes). Visualization of the internalized antibodies was performed as described above.

In Vitro Proliferation Assay (MTT Assay).

Cell lines were plated at a density of 2500 cells/well in 96-well plates and allowed to recover overnight in phenol red-free Iscove's modified Dulbecco's medium (IMDM) containing 10% FBS and supplements (growth medium). Cells were challenged for 1 h with mAb or ADC (twice in a volume of 50 µl) in IMDM at the indicated concentrations. Cells were then washed twice with growth medium and allowed to proliferate in fresh growth medium for 4 days, cell viability was then assessed by the CellTiter 96™ AQueous Non-Radioactive Cell Proliferation Assay (Promega), as per the manufacturer's instructions. All growth studies were performed at least three times in triplicate.

Results

FIG. 5 depicts a table showing the compiled results on 42 mAbs (including GPR64-18 described in Example 2). The results include various measures of antibody binding affinity including FACS titration (i.e. $EC_{50}$), surface plasmon resonance (i.e. Biacore®), immunohistochemical (IHC) and immunofluorescence (IF). Interestingly, many of these monoclonal antibodies are IgG2a and IgG2b isotype. More importantly, many of these antibodies exhibit low $EC_{50}$ values by FACS assay, and nanomolar or subnanomolar $K_D$ values by Biacore®.

The immunofluorescence (IF) assays showed cell surface staining that was also confirmed by FACS assay. Significantly, the IF assay designed to visualize internalization of GPR64 monoclonal antibodies showed a shift of fluorescent staining from the cell surface to the cell interior. This result confirms that GPR64 mAbs are internalized, which is critical for using these mAbs in an antibody-drug conjugate (ADC) approach to therapy.

Thus, a large number of purified anti-GPR64 monoclonal antibodies have been generated that exhibit desirable binding properties for use as possible antibody therapeutics in targeting tumor growth and other proliferative disorders associated with GPR64 expression. The purified GPR64 mAbs were also assessed for effects on growth in vitro using a standard 4-day MTT assay. The results show that the purified mAbs alone have little or no effect on cell growth in this in vitro assay. However, as described in Example 2 and below, effects on growth can be detected with in vivo assays.

Example 5

IHC Validation of GPR64 as an Ovarian Cancer Target

Tissue microarrays of normal tissues and ovarian cancer samples were obtained from Clinomics Biosciences, Inc. (Pittsfield, Mass.). IHC on formalin-fixed paraffin embedded tissues was carried out using standard methods as previously described (Henshall et al., 2003, Oncogene 22:6005-6012). Heat induced antigen retrieval was performed in Dako Target Retrieval Solution for 15 minutes in a pressure cooker. Samples were then incubated with a GPR64 specific antibody (e.g. GPR64-101) or control mouse IgG1 [TIB191, a mouse anti-trinitrophenol mAb (hybridoma clone 1B76.11, ATCC)] for 30 minutes. Antibody binding was detected using biotinylated secondary antibody [Goat-anti-mouse IgG (3 mg/ml, 30 minutes; Jackson ImmunoResearch)], and developed using the VECTASTAIN® Elite ABC Kit (Vector Laboratories) and stable DAB (diaminobenzidine and H2O2; Research Genetics). Staining was performed using the DAKO Autostainer at room temperature.

Figure 6:
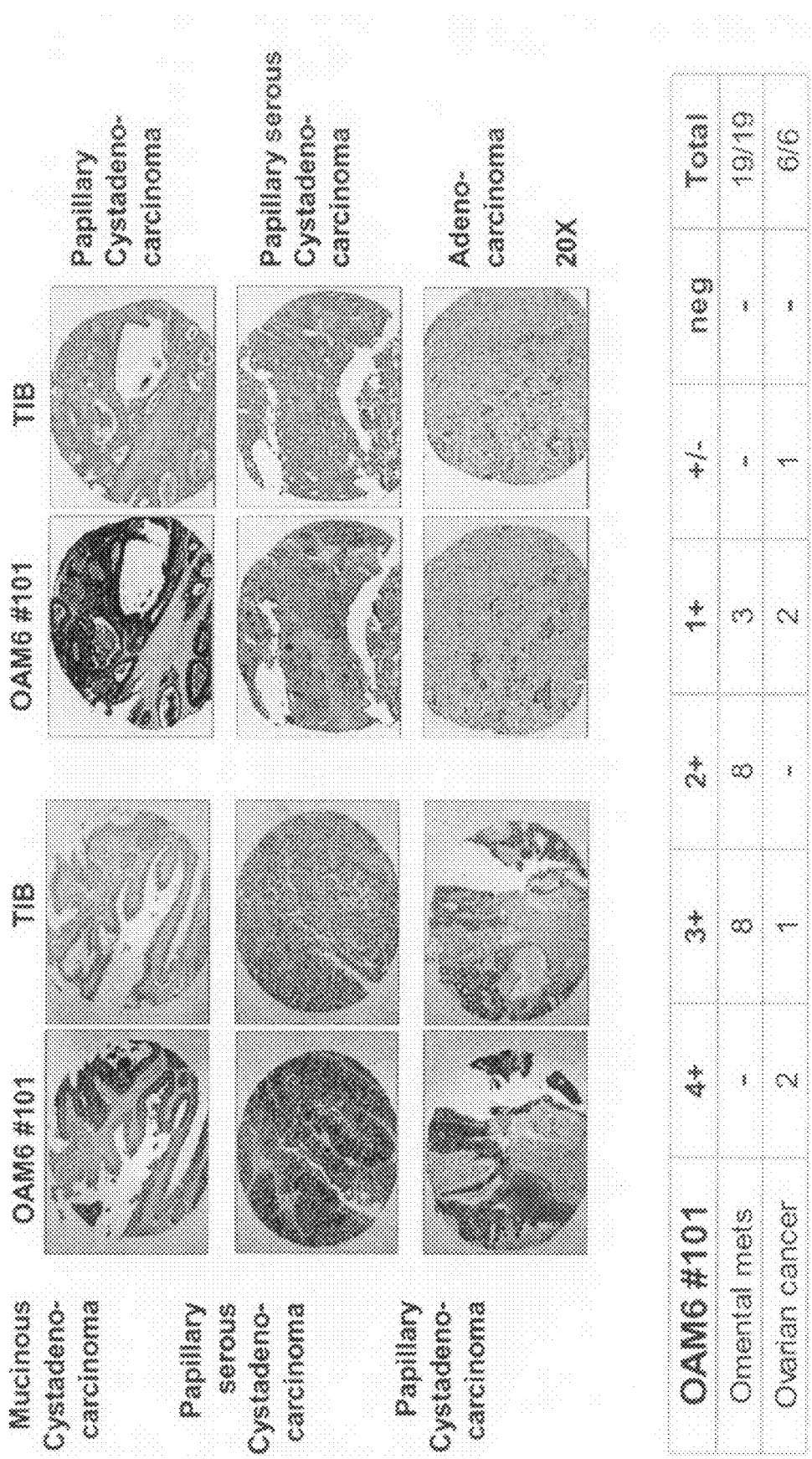
FIG. 6 depicts images of immunohistochemical staining of various ovarian cancer tissue samples with the monoclonal antibody GPR64-101.

As shown in FIG. 6, IHC staining of various ovarian cancer samples with antibody GPR64-101 (OAM6#101 in figure)

revealed high expression of GPR64. Equally important, as shown in FIG. 7, GPR64-101 (OAM6#101 in figure) did not significantly stain any of the normal tissues tested, with the exception of some staining of parathyroid glands.

Figure 7:
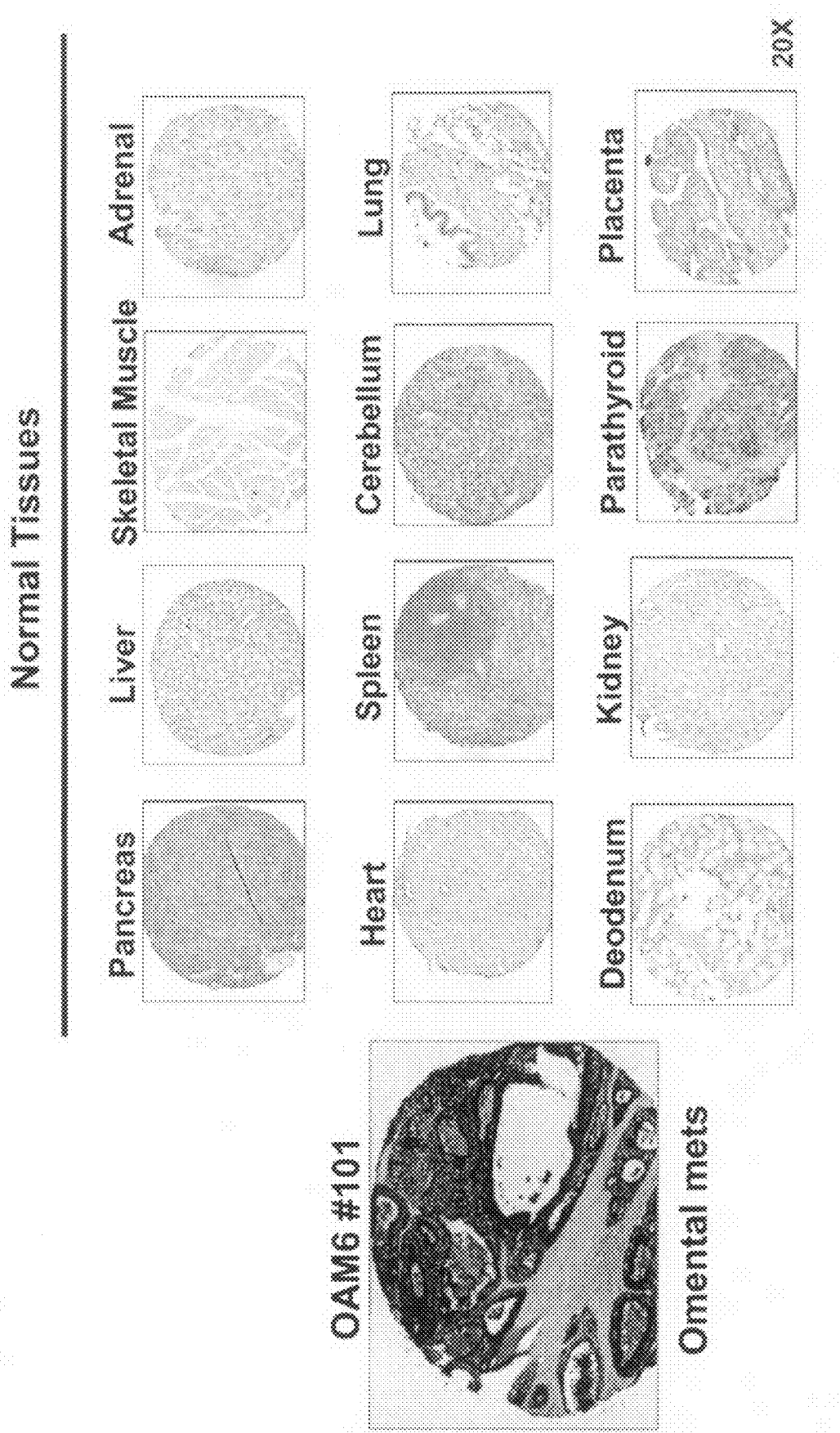
FIG. 7 depicts images of immunohistochemical staining of various normal tissue samples with the monoclonal antibody GPR64-101.

The data shown in FIGS. 6 and 7 agree with the expression profile of GPR64 determined using oligonucleotide microarrays (GeneChip) and confirms that GPR64 is highly expressed in ovarian cancer relative to the normal body atlas. Consequently, these IHC studies further validate GPR64 as an ovarian cancer target.

Example 6

Effect of Purified Anti-GPR64 mAbs in H460 Xenograft Treatment Model In Vivo

Purified GPR64 mAbs that exhibited high affinity (GPR64-18, GPR64-61, GPR64-62, GPR64-81, GPR64-93, and GPR64-95) were tested on the in vivo H460 xenograft model according to the same general method described in Example 2. H460 tumors were allowed to reach ~100 mm$^3$ in size before treatment with 10 mg/kg of purified naked GPR64 antibody, or a TIB191 isotype control.

Figure 8:
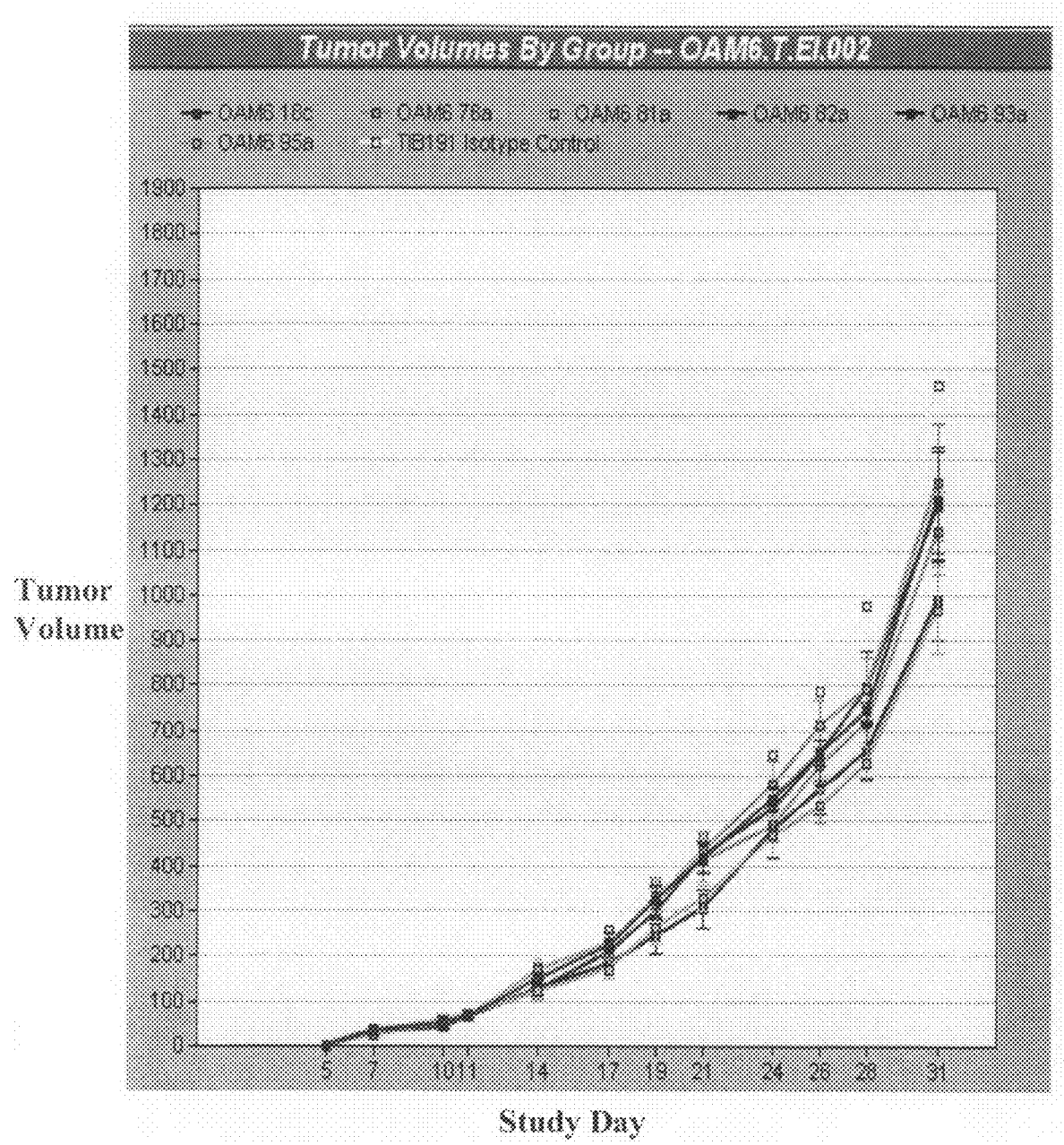
FIG. 8 depicts plots of tumor growth over the course of an in vivo H460 xenografts with various GPR64 monoclonal antibodies.

As shown in FIG. 8, although none of the antibodies completely abolish tumor growth in H460 xenografts, the higher affinity antibodies GPR64-81 (OAM6#81a in figure) and GPR64-93 (OAM6#93a in figure) exhibited better in vivo efficacy at slowing growth.

Example 7

Epitope Mapping of Purified GPR64 mAbs

Epitope mapping was performed by competitive FACS assay. Briefly, H460 cells were incubated with 25 ug/ml unlabeled antibody for 1 hr on ice, at which time various amounts of FITC labeled antibody was added. After 30 additional minutes, cells were washed one time and fluorescence was measured by flow cytometry. All data was confirmed by Biacore®.

Results identify four distinct epitopes. Interestingly, the two anti-GPR64 mAbs (GPR64-81, and GPR64-93) exhibiting the greatest in vivo efficacy recognize two different epitopes on GPR64. GPR64-101 also binds to its own distinct epitope, but GPR64-18, -61, -62, -65, -95, and -99 all bind to the same epitope.

Example 8

Cell-Based Immunizations

Cell-based immunizations using transfectants in the Balb/c syngeneic cell line 3T12 have been used to generate mAbs to the full-length GPR64 antigen. However, the low wild-type expression of GPR64 and high 3T12 background titer, generally resulted in low GPR64 specific titers. In order to increase GPR64 specific titers, a DRY box mutant of GPR64 in 3T12 was engineered. The DRY box motif is involved in coupling GPR64 to its signaling G protein. It is believed that the DRY box mutant uncouples this signaling mechanism and thereby permits increased GPR64 expression. It was found by FACS analysis that the DRY box mutant engineered 3T12 exhibited GPR64 expression at 20-fold higher levels than in the wild-type cells. DRY box mutants of 3T12 were used in a passive immunization strategy. The resulting serum titers for GPR64 were much higher and exhibited less background than the original wild-type cell-based immunizations.

Using the above-described combination of DRY box mutants and passive immunization one may produce panels of GPR64 mAbs to the full length protein that may exhibit much improved binding affinities and efficacy in tumor growth inhibition.

Example 9

GPR64 Antibody Drug Conjugates on H460 Cells

GPR64 antibodies were coupled to the microtubule toxin Auristatin E (VCAE) and tested for their ability to kill H460 cells in vitro.

Anti-GPR64-VC-MMAE (valine-citrulline linked monomethyl auristatin E) ADC was prepared as described previously (Doronina et al., 2003, Nat. Biotechnol. 21:778-784). In brief, a purified anti-GPR64 mAb or a control isotype (TIB191) was reduced with 10 mM DTT, and thiol content was determined by measuring A412 after incubation with Ellman's reagent and subsequent calculation. Equimolar maleimide-VC-MMAE solution [8 mM in DMSO (Sigma)] in cold acetonitrile (20% final concentration) was incubated with reduced mAb for 30 min at 4° C. Unconjugated VC-MMAE was removed by dialysis at 4° C. into PBS and filtered. Conjugated mAb was quantified using A280/A260, and the extent of aggregate versus monomer was determined by size-exclusion high-performance liquid chromatography. Finally, matrix assisted laser desorption ionization-time of flight mass spectrometry was used to determine the number of drug molecules per mAb.

As shown in FIG. 9, a panel of 18 different GPR64 mAb-VCAE conjugates were tested against H460 cells in a 4-day MTT assay (as described in Example 4 above). Results show that a subset of GPR64 mAb ADCs including GPR64-18, -81, -82, -93, and -95 significantly inhibit H460 cell survival.

Figure 10:
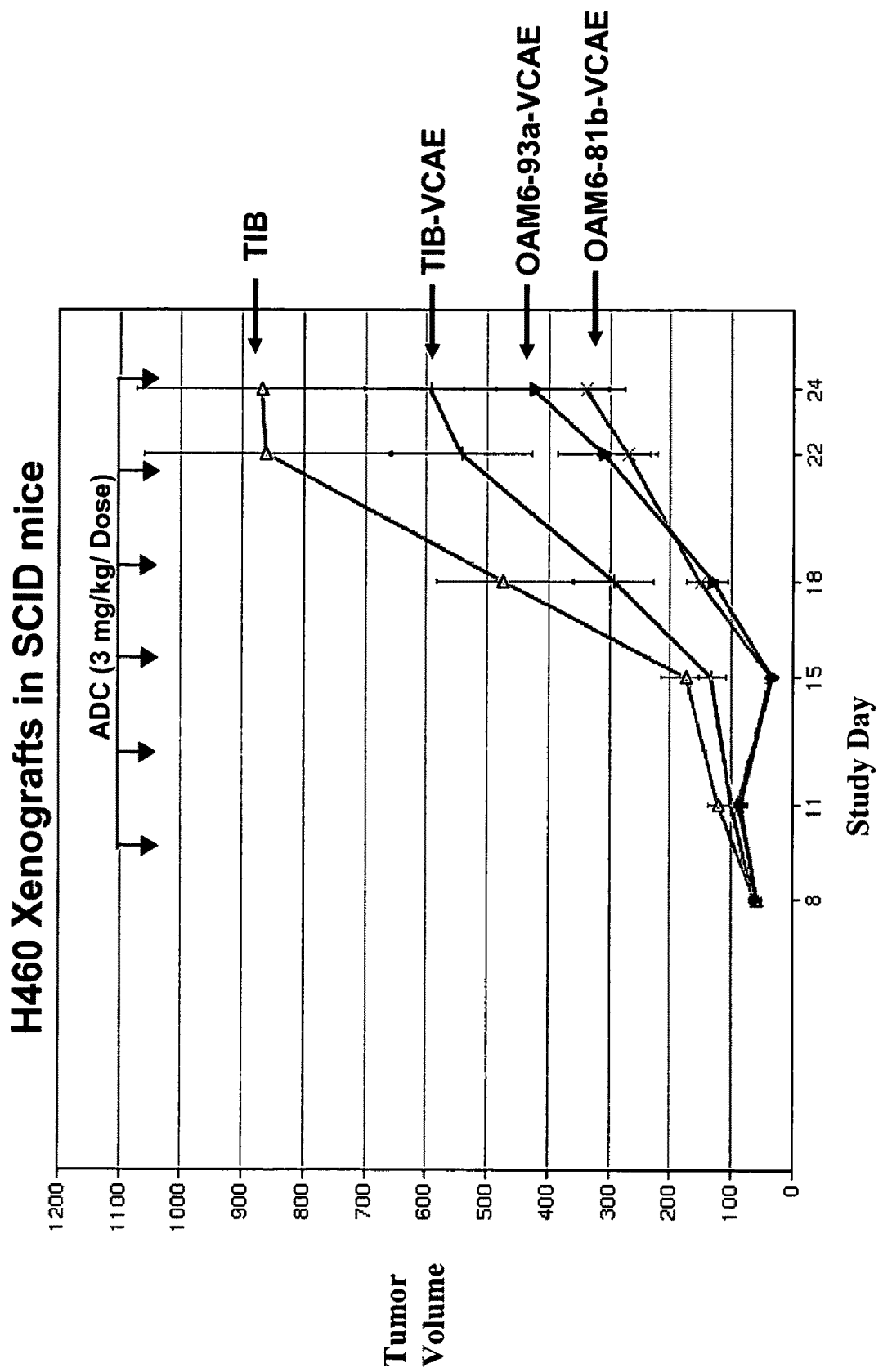
FIG. 10 depicts a plot of in vivo H460 tumor growth during a dosing regimen with GPR64-81, and -93 mAb-VCAE conjugates.

Two of the above ADCs GPR64-81 and GPR64-93 were further tested for inhibition of H460 xenograft growth in vivo according to the method described above in Example 6. As shown in FIG. 10, both GPR64-VCAE ADCs significantly slow tumor growth, but neither has a complete effect.

It is understood that the examples described above in no way serve to limit the true scope of this invention, but rather are presented for illustrative purposes. All publications, sequences of accession numbers, and patent applications cited in this specification are herein incorporated by reference as if each individual publication or patent application were specifically and individually indicated to be incorporated by reference.

All UniGene cluster identification numbers and accession numbers herein are for the GenBank® sequence database and the sequences of the accession numbers are hereby expressly incorporated by reference. GenBank® is known in the art, see, e.g., Benson, D A, et al., Nucleic Acids Research 26:1-7 (1998). Sequences are also available in other databases, e.g. European Molecular Biology Laboratory (EMBL) and DNA Database of Japan (DDBJ).

Deposit of Material

The following material has been deposited with the American Type Culture Culture Collection, 10801 University Blvd., Manassas, Va. 20110-2209, USA (ATCC):

| Material | ATCC Dep. No. | Deposit Date |
| --- | --- | --- |
| Hybridoma OAM6#81 (produces GPR64-81 mAb) | PTA-5703 | Dec. 19, 2003 |

| Material | ATCC Dep. No. | Deposit Date |
|---|---|---|
| Hybridoma OAM6#93 (produces GPR64-93 mAb) | PTA-5704 | Dec. 19, 2003 |

This deposit was made under the provisions of the Budapest Treaty on the International Recognition of the Deposit of Microorganisms for the purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Protein Design Labs, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trade to be entitled thereto according to 35 U.S.C. § 122 and the Commissioner's rules pursuant thereto (including 37 CFR § 1.14 with particular reference to 886 OG 638). All restrictions upon public access to the deposit will be irrevocably removed upon the grant of a patent on this application.

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the right granted under the authority of any government in accordance with its patent laws.

The present invention should not to be limited in scope by the construct deposited, since the deposited embodiment is intended as a single illustration of certain aspects of the invention and any constructs that are functionally equivalent are within the scope of the this invention.

What is claimed:

1. A hybridoma cell line deposited as ATCC Accession Number PTA-5703.

2. An antibody produced by a hybridoma cell line having ATCC Accession number PTA-5703.

3. An antigen binding fragment of the antibody of claim 2.

4. The antigen binding fragment of claim 3, selected from the group consisting of Fab, Fab', F(ab')2, and Fv fragments.

5. A conjugate comprising the antibody of claim 2, wherein the antibody is conjugated to an effector moiety and binds to a polypeptide comprising the amino acid sequence of SEQ ID NO: 2.

6. The conjugate of claim 5, wherein the effector moiety is selected from the group consisting of: a fluorescent label, a radioisotope, and a cytotoxic agent.

7. The conjugate of claim 6, wherein the cytotoxic agent is selected from the group consisting of: diphtheria A chain, exotoxin A chain, ricin A chain, abrin A chain, curcin, crotin, phenomycin, neomycin, and auristatin.

8. The conjugate of claim 6, wherein the cytotoxic agent is auristatin.

9. The conjugate of claim 6, wherein the radioisotope is selected from the group consisting of $^3H$, $^{14}C$, $^{32}P$, $^{35}S$, $^{125}I$, $^{113}I$, $Y^{90}$ and $Re^{186}$.

10. The antibody of claim 2, wherein the antibody binds a polypeptide having the amino acid sequence of SEQ ID NO:2.

11. The antibody of claim 10, wherein the polypeptide is localized to the cell surface of a cancer cell.

12. The antibody of claim 11, wherein the antibody inhibits growth of the cancer cell upon binding to the cell.

13. A pharmaceutical composition comprising a pharmaceutically acceptable excipient and the antibody of claim 2.

14. A pharmaceutical composition comprising a pharmaceutically acceptable excipient and the conjugate of claim 8.

15. A diabody comprising a first polypeptide comprising the heavy chain variable domain (VH) of the antibody of claim 2 and further comprising a second polypeptide comprising the light chain variable domain (VL) of the antibody of claim 2, wherein said diabody comprises an antigen binding domain that binds to a polypeptide comprising the amino acid sequence of SEQ ID NO:2.

16. A single chain antibody comprising the heavy chain variable domain (VH) of the antibody of claim 2 and the light chain variable domain (VL) of the antibody of claim 2, wherein said single chain antibody binds to a polypeptide comprising the amino acid sequence of SEQ ID NO:2.

17. A chimeric antibody comprising a first polypeptide comprising the heavy chain variable domain (VH) of the antibody of claim 2 and further comprising a second polypeptide comprising the light chain variable domain (VL) of the antibody of claim 2, wherein said chimeric antibody binds to a polypeptide comprising the amino acid sequence of SEQ ID NO:2.

18. A humanized antibody comprising a first polypeptide comprising each of the three complementarity determining regions (CDRs) of the heavy chain variable domain (VH) of the antibody of claim 2 and further comprising a second polypeptide comprising each of the three CDRs of the light chain variable domain (VL) of the antibody of claim 2, wherein said humanized antibody binds to a polypeptide comprising the amino acid sequence of SEQ ID NO:2.

* * * * *

SEQUENCE LISTING

```
<160> NUMBER OF SEQ ID NOS: 30

<210> SEQ ID NO 1
<211> LENGTH: 4665
<212> TYPE: DNA
<213> ORGANISM: Homo sapiens

<400> SEQUENCE: 1
agccagcccg aggacgcgag cggcaggtgt gcacagaggt tctccacttt gttttctgaa      60
ctcgcggtca ggatggtttt ctctgtcagg cagtgtggcc atgttggcag aactgaagaa     120
gttttactga cgttcaagat attccttgtc atcatttgtc ttcatgtcgt tctggtaaca     180
tccctggaag aagatactga taattccagt ttgtcaccac cacctgctaa attatctgtt     240
gtcagttttg ccccctcctc caatgaggtt gaaacaacaa gcctcaatga tgttacttta     300
agcttactcc cttcaaacga aacagaaaaa actaaaatca ctatagtaaa aaccttcaat     360
gcttcaggcg tcaaacccca gagaaatatc tgcaatttgt catctatttg caatgactca     420
gcatttttta gaggtgagat catgtttcaa tatgataaag aaagcactgt tccccagaat     480
caacatataa cgaatggcac cttaactgga gtcctgtctc taagtgaatt aaaacgctca     540
gagctcaaca aaaccctgca aaccctaagt gagacttact ttataatgtg tgctacagca     600
gaggcccaaa gcacattaaa ttgtacattc acaataaaac tgaataatac aatgaatgca     660
tgtgctgcaa tagccgcttt ggaaagagta aagattcgac caatggaaca ctgctgctgt     720
tctgtcagga taccctgccc ttcctcccca gaagagttgg gaaagcttca gtgtgacctg     780
caggatccca ttgtctgtct tgctgaccat ccacgtggcc caccattttc ttccagccaa     840
tccatcccag tggtgcctcg ggccactgtg ctttcccagg tccccaaagc tacctctttt     900
gctgagcctc cagattattc acctgtgacc cacaatgttc cctctccaat aggggagatt     960
caaccccttt caccccagcc ttcagctccc atagcttcca gccctgccat tgacatgccc    1020
ccacagtctg aaacgatctc ttcccctatg ccccaaaccc atgtctccgg caccccacct    1080
cctgtgaaag cctcatttc ctctcccacc gtgtctgccc ctgcgaatgt caacactacc    1140
agcgcacctc ctgtccagac agacatcgtc aacaccagca gtatttctga tcttgagaac    1200
caagtgttgc agatggagaa ggctctgtcc ttgggcagcc tggagcctaa cctcgcagga    1260
```

```
gaaatgatca accaagtcag cagactcctt cattccccgc ctgacatgct ggcccctctg   1320
gctcaaagat tgctgaaagt agtggatgac attggcctac agctgaactt ttcaaacacg   1380
actataagtc taacctcccc ttctttggct ctggctgtga tcagagtgaa tgccagtagt   1440
ttcaacacaa ctacctttgt ggcccaagac cctgcaaatc ttcaggtttc tctggaaacc   1500
caagctcctg agaacagtat tggcacaatt actcttcctt catcgctgat gaataattta   1560
ccagctcatg acatggagct agcttccagg gttcagttca attttttga aacacctgct    1620 ttgtttcagg atccttccct ggagaacctc tctctgatca gctacgtcat atcatcgagt   1680
gttgcaaacc tgaccgtcag gaacttgaca agaaacgtga cagtcacatt aaagcacatc   1740
aacccgagcc aggatgagtt aacagtgaga tgtgtatttt gggacttggg cagaaatggt   1800
ggcagaggag gctggtcaga caatggctgc tctgtcaaag acaggagatt gaatgaaacc   1860
atctgtacct gtagccatct aacaagcttc ggcgttctgc tggacctatc taggacatct   1920
gtgctgcctg ctcaaatgat ggctctgacg ttcattacat atattggttg tgggctttca   1980
tcaatttttc tgtcagtgac tcttgtaacc tacatagctt ttgaaaagat ccggagggat   2040
tacccttcca aaatcctcat ccagctgtgt gctgctctgc ttctgctgaa cctggtcttc   2100
ctcctggact cgtggattgc tctgtataag atgcaaggcc tctgcatctc agtggctgta   2160
tttcttcatt attttctctt ggtctcattc acatggatgg gcctagaagc attccatatg   2220
tacctggccc ttgtcaaagt atttaatact tacatccgaa aatacatcct taaattctgc   2280
attgtcggtt ggggggtacc agctgtggtt gtgaccatca tcctgactat atccccagat   2340
aactatgggc ttggatccta tgggaaattc cccaatggtt caccggatga cttctgctgg   2400
atcaacaaca atgcagtatt ctacattacg gtggtgggat attttgtgt gatatttttg    2460 ctgaacgtca gcatgttcat tgtggtcctg gttcagctct gtcgaattaa aaagaagaag   2520
caactgggag cccagcgaaa aaccagtatt caagacctca ggagtatcgc tggccttaca   2580
tttttactgg gaataacttg gggctttgcc ttctttgcct ggggaccagt taacgtgacc   2640
ttcatgtatc tgtttgccat ctttaatacc ttacaaggat ttttcatatt catcttttac   2700
tgtgtggcca agaaaatgt caggaagcaa tggaggcggt atctttgttg tggaaagtta    2760
cggctggctg aaaattctga ctggagtaaa actgctacta atggtttaaa gaagcagact   2820
gtaaaccaag gagtgtccag ctcttcaaat tccttacagt caagcagtaa ctccactaac   2880
tccaccacac tgctagtgaa taatgattgc tcagtacacg caagcgggaa tggaaatgct   2940
tctacagaga ggaatggggt ctcttttagt gttcagaatg gagatgtgtg ccttcacgat   3000
ttcactggaa aacagcacat gtttaacgag aaggaagatt cctgcaatgg aaaggccgt    3060 atggctctca gaaggacttc aaagcgggga agcttacact ttattgagca aatgtgattc   3120
ctttcttcta aaatcaaagc atgatgcttt acagtgtgaa atgtccaatt ttaccttta    3180 cacaatgtga gatgtatgaa aatcaactca ttttattctc ggcaacatct ggagaagcat   3240
aagctaatta agggcgatga ttattattac aagaagaaac caagacatta caccatggtt   3300
tttagacatt tctgatttgg tttcttatct ttcattttat aagaaggttg gttttaaaca   3360
atacactaag aatgactcct ataaagaaaa caaaaaaagg tagtgaactt tcagctacct   3420
tttaaagagg ctaagttatc tttgataaca tcatataaag caactgttga cttcagcctg   3480
ttggtgagtt tagttgtgca tgcctttgtt gtatataagc taaattctag tgacccatgt   3540
gtcaaaaatc ttacttctac attttttgt atttattttc tactgtgtaa atgtattcct    3600
```

-continued

```
ttgtagaatc atggttgttt tgtctcacgt gataattcag aaaatccttg ctcgttccgc   3660
aaatcctaaa gctccttttg gagatgatat aggatgtgaa atacagaaac ctcagtgaaa   3720
tcaagaaata atgatcccag ccagactgag aaaatgtaag cagacagtgc cacagttagc   3780
tcatacagtg cctttgagca agttaggaaa agatgccccc actgggcaga cacagcccta   3840
tgggtcatgg tttgacaaac agagtgagag accatatttt agccccactc accctcttgg   3900
gtgcacgacc tgtacagcca acacagcat  ccaatatgaa tacccatccc ctgaccgcat   3960
ccccagtagt cagattatag aatctgcacc aagatgttta gctttatacc ttggccacag   4020
agagggatga actgtcatcc agaccatgtg tcaggaaaat tgtgaacgta gatgaggtac   4080
atacactgcc gcttctcaaa tccccagagc ctttaggaac aggagagtag actaggattc   4140
cttctcttaa aaaggtacat atatatgaa  aaaaatcata ttgccgttct ttaaaaggca   4200
actgcatggt acattgttga ttgttatgac tggtacactc tggcccagcc agagctataa   4260 ttgttttta  aatgtgtctt gaagaatgca cagtgacaag gggagtagct attgggaaca   4320
gggaactgtc ctacactgct attgttgcta catgtatcga gccttgattg ctcctagtta   4380
tatacagggt ctatcttgct tcctacctac atctgcttga gcagtgcctc aagtacatcc   4440
ttattaggaa catttcaaac ccctttagt  taagtctttc actaaggttc tcttgcatat   4500
atttcaagtg aatgttggat ctcagactaa ccatagtaat aatacacatt tctgtgagtg   4560
ctgacttgtc tttgcaatat ttcttttctg atttatttaa ttttcttgta tttatatgtt   4620
aaaatcaaaa atgttaaaat caatgaaata aatttgcagt taaga              4665
```

```
<210> SEQ ID NO 2
<211> LENGTH: 1014
<212> TYPE: PRT
<213> ORGANISM: Homo Sapiens

<400> SEQUENCE: 2
```

```
Met Val Phe Ser Val Arg Gln Cys Gly His Val Gly Arg Thr Glu Glu
1               5                   10                  15

Val Leu Leu Thr Phe Lys Ile Phe Leu Val Ile Ile Cys Leu His Val
            20                  25                  30

Val Leu Val Thr Ser Leu Glu Glu Asp Thr Asp Asn Ser Ser Leu Ser
        35                  40                  45

Pro Pro Ala Lys Leu Ser Val Val Ser Phe Ala Pro Ser Ser Asn
50                  55                  60

Glu Val Glu Thr Thr Ser Leu Asn Asp Val Thr Leu Ser Leu Leu Pro
65                  70                  75                  80

Ser Asn Glu Thr Glu Lys Thr Lys Ile Thr Ile Val Lys Thr Phe Asn
                85                  90                  95

Ala Ser Gly Val Lys Pro Gln Arg Asn Ile Cys Asn Leu Ser Ser Ile
            100                 105                 110

Cys Asn Asp Ser Ala Phe Phe Arg Gly Glu Ile Met Phe Gln Tyr Asp
        115                 120                 125

Lys Glu Ser Thr Val Pro Gln Asn Gln His Ile Thr Asn Gly Thr Leu
    130                 135                 140

Thr Gly Val Leu Ser Leu Ser Glu Leu Lys Arg Ser Glu Leu Asn Lys
145                 150                 155                 160

Thr Leu Gln Thr Leu Ser Glu Thr Tyr Phe Ile Met Cys Ala Thr Ala
                165                 170                 175

Glu Ala Gln Ser Thr Leu Asn Cys Thr Phe Thr Ile Lys Leu Asn Asn
            180                 185                 190
```

```
Thr Met Asn Ala Cys Ala Ala Ile Ala Ala Leu Glu Arg Val Lys Ile
        195                 200                 205

Arg Pro Met Glu His Cys Cys Ser Val Arg Ile Pro Cys Pro Ser
210                 215                 220

Ser Pro Glu Glu Leu Gly Lys Leu Gln Cys Asp Leu Gln Asp Pro Ile
225                 230                 235                 240

Val Cys Leu Ala Asp His Pro Arg Gly Pro Phe Ser Ser Ser Gln
            245                 250                 255

Ser Ile Pro Val Val Pro Arg Ala Thr Val Leu Ser Gln Val Pro Lys
            260                 265                 270

Ala Thr Ser Phe Ala Glu Pro Asp Tyr Ser Pro Val Thr His Asn
        275                 280                 285

Val Pro Ser Pro Ile Gly Glu Ile Gln Pro Leu Ser Pro Gln Pro Ser
        290                 295                 300

Ala Pro Ile Ala Ser Pro Ala Ile Asp Met Pro Pro Gln Ser Glu
305                 310                 315                 320

Thr Ile Ser Ser Pro Met Pro Gln Thr His Val Ser Gly Thr Pro Pro
                325                 330                 335

Pro Val Lys Ala Ser Phe Ser Ser Pro Thr Val Ser Ala Pro Ala Asn
            340                 345                 350

Val Asn Thr Thr Ser Ala Pro Pro Val Gln Thr Asp Ile Val Asn Thr
        355                 360                 365

Ser Ser Ile Ser Asp Leu Glu Asn Gln Val Leu Gln Met Glu Lys Ala
370                 375                 380

Leu Ser Leu Gly Ser Leu Glu Pro Asn Leu Ala Gly Glu Met Ile Asn
385                 390                 395                 400

Gln Val Ser Arg Leu Leu His Ser Pro Pro Asp Met Leu Ala Pro Leu
                405                 410                 415

Ala Gln Arg Leu Leu Lys Val Val Asp Asp Ile Gly Leu Gln Leu Asn
            420                 425                 430

Phe Ser Asn Thr Thr Ile Ser Leu Thr Ser Pro Ser Leu Ala Leu Ala
        435                 440                 445

Val Ile Arg Val Asn Ala Ser Ser Phe Asn Thr Thr Thr Phe Val Ala
450                 455                 460

Gln Asp Pro Ala Asn Leu Gln Val Ser Leu Thr Gln Ala Pro Glu
465                 470                 475                 480

Asn Ser Ile Gly Thr Ile Thr Leu Pro Ser Ser Leu Met Asn Asn Leu
            485                 490                 495

Pro Ala His Asp Met Glu Leu Ala Ser Arg Val Gln Phe Asn Phe Phe
        500                 505                 510

Glu Thr Pro Ala Leu Phe Gln Asp Pro Ser Leu Glu Asn Leu Ser Leu
    515                 520                 525

Ile Ser Tyr Val Ile Ser Ser Val Ala Asn Leu Thr Val Arg Asn
        530                 535                 540

Leu Thr Arg Asn Val Thr Val Thr Leu Lys His Ile Asn Pro Ser Gln
545                 550                 555                 560

Asp Glu Leu Thr Val Arg Cys Val Phe Trp Asp Leu Gly Arg Asn Gly
            565                 570                 575

Gly Arg Gly Gly Trp Ser Asp Asn Gly Cys Ser Val Lys Asp Arg Arg
            580                 585                 590

Leu Asn Glu Thr Ile Cys Thr Cys Ser His Leu Thr Ser Phe Gly Val
            595                 600                 605
```

-continued

```
Leu Leu Asp Leu Ser Arg Thr Ser Val Leu Pro Ala Gln Met Met Ala
    610                 615                 620
Leu Thr Phe Ile Thr Tyr Ile Gly Cys Gly Leu Ser Ser Ile Phe Leu
625                 630                 635                 640
Ser Val Thr Leu Val Thr Tyr Ile Ala Phe Glu Lys Ile Arg Arg Asp
                645                 650                 655
Tyr Pro Ser Lys Ile Leu Ile Gln Leu Cys Ala Ala Leu Leu Leu Leu
            660                 665                 670
Asn Leu Val Phe Leu Leu Asp Ser Trp Ile Ala Leu Tyr Lys Met Gln
        675                 680                 685
Gly Leu Cys Ile Ser Val Ala Val Phe Leu His Tyr Phe Leu Leu Val
    690                 695                 700
Ser Phe Thr Trp Met Gly Leu Glu Ala Phe His Met Tyr Leu Ala Leu
705                 710                 715                 720
Val Lys Val Phe Asn Thr Tyr Ile Arg Lys Tyr Ile Leu Lys Phe Cys
                725                 730                 735
Ile Val Gly Trp Gly Val Pro Ala Val Val Thr Ile Ile Leu Thr
            740                 745                 750
Ile Ser Pro Asp Asn Tyr Gly Leu Gly Ser Tyr Gly Lys Phe Pro Asn
        755                 760                 765
Gly Ser Pro Asp Asp Phe Cys Trp Ile Asn Asn Asn Ala Val Phe Tyr
    770                 775                 780
Ile Thr Val Val Gly Tyr Phe Cys Val Ile Phe Leu Leu Asn Val Ser
785                 790                 795                 800
Met Phe Ile Val Val Leu Val Gln Leu Cys Arg Ile Lys Lys Lys Lys
                805                 810                 815
Gln Leu Gly Ala Gln Arg Lys Thr Ser Ile Gln Asp Leu Arg Ser Ile
            820                 825                 830
Ala Gly Leu Thr Phe Leu Leu Gly Ile Thr Trp Gly Phe Ala Phe Phe
        835                 840                 845
Ala Trp Gly Pro Val Asn Val Thr Phe Met Tyr Leu Phe Ala Ile Phe
    850                 855                 860
Asn Thr Leu Gln Gly Phe Phe Ile Phe Ile Phe Tyr Cys Val Ala Lys
865                 870                 875                 880
Glu Asn Val Arg Lys Gln Trp Arg Arg Tyr Leu Cys Cys Gly Lys Leu
                885                 890                 895
Arg Leu Ala Glu Asn Ser Asp Trp Ser Lys Thr Ala Thr Asn Gly Leu
            900                 905                 910
Lys Lys Gln Thr Val Asn Gln Gly Val Ser Ser Ser Asn Ser Leu
        915                 920                 925
Gln Ser Ser Ser Asn Ser Thr Asn Ser Thr Thr Leu Leu Val Asn Asn
    930                 935                 940
Asp Cys Ser Val His Ala Ser Gly Asn Gly Asn Ala Ser Thr Glu Arg
945                 950                 955                 960
Asn Gly Val Ser Phe Ser Val Gln Asn Gly Asp Val Cys Leu His Asp
                965                 970                 975
Phe Thr Gly Lys Gln His Met Phe Asn Glu Lys Glu Asp Ser Cys Asn
            980                 985                 990
Gly Lys Gly Arg Met Ala Leu Arg Arg Thr Ser Lys Arg Gly Ser Leu
        995                 1000                1005
His Phe Ile Glu Gln Met
    1010
```

<210> SEQ ID NO 3
<211> LENGTH: 339
<212> TYPE: DNA
<213> ORGANISM: Mus sp.

<400> SEQUENCE: 3

```
gatgtgcagc ttcaggagtc gggacctggc ctggtgaaac cttctcagtc tctgtccctc      60
acctgcactg tcactggcta ctcaatcacc agtgattatg cctggaactg gatccggcag     120
tttccaggaa acaaactgga gtggctgggc tacataagct tcaatgataa cactaactac     180
aacccatctc tcaaaagtcg aatctctatc actcgagaca catccaagaa ccagttcttc     240
ctgcagttga attctgtgac tactgaggac acagccacat attactgtac aaggagggtg     300
gactactggg gtcaaggaac ctcagtcacc gtctcctca                             339
```

<210> SEQ ID NO 4
<211> LENGTH: 336
<212> TYPE: DNA
<213> ORGANISM: Mus sp.

<400> SEQUENCE: 4

```
gatgttgtga tgacccaaac tccactctcc ctgcctgtca gtcttggaga tcaagcctcc      60
atctcttgca gatctagtca gagccttgta cacagtaatg aaacaactat tttacattgg     120
tatttgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttccg     300
tggacgttcg gtggaggcac caagctggaa atcaaa                                336
```

<210> SEQ ID NO 5
<211> LENGTH: 360
<212> TYPE: DNA
<213> ORGANISM: Mus sp.

<400> SEQUENCE: 5

```
caggttactc tgaaagagtc tggccctggg atattgcagc cctcccagac cctcagtctg      60
acttgttctt tctctgggtt ttcactgagc acttctggtg tgggtgtgag ctggattcgt     120
cagccttcag gaaagggtct ggagtggctg gcacacattt actgggatga tgataagcgc     180
tataacccat ccctgaagag ccggctcaca atctccaagg atacctccag aaaccaggta     240
ttcctcaaga tcaccagtgt ggacactgca gatactgcca catactactg tgctcgaaga     300
gtattcatta ttacggcctt tgactactgg ggccaaggca ccactctcac agtctcctca     360
```

<210> SEQ ID NO 6
<211> LENGTH: 321
<212> TYPE: DNA
<213> ORGANISM: Mus sp.

<400> SEQUENCE: 6

```
gatatccaga tgacacagac tacatcctcc ctgtctgcct ctctgggaga cagagtcacc      60
atcagttgca gggcaagtca ggacattagc aattacttaa actggtatca gcagaaacca     120
gatggaactg ttaaactcct gatctactac acatcaaact acactcagg agtcccatca     180
aggttcagtg gcagtgggtc tggagcagat tattctctca ccattggcaa cctggagcaa     240
gaagatattg ccacttactt ttgccaacag ggtaatacgc ttccttggac gttcggtgga     300
ggcaccaagc tggaaatcaa a                                                321
```

<210> SEQ ID NO 7
<211> LENGTH: 366
<212> TYPE: DNA
<213> ORGANISM: Mus sp.

<400> SEQUENCE: 7

| caggtttctc | tgaaagagtc | tggccctggg | atattgcagc | cctcccagac | cctcagtctg | 60 |
| acttgttctt | tctctgggtt | ttcactgagc | acttctggta | tgggtgtgag | ctggattcgt | 120 |
| cagccttcag | gaaagggtct | ggagtggctg | gcacacattt | actgggatga | tgacaagcgc | 180 |
| tataacccat | ccctgaagag | ccggctcaca | atctccaagg | atacctccag | caacctggta | 240 |
| ttcctcaaga | tcaccagtgt | ggacactgca | gatactgcca | catactactg | tgctcgaagg | 300 |
| gaagtacgac | gtgattacta | tgctatggac | tactggggtc | aaggaacctc | agtcaccgtc | 360 |
| tcctca | | | | | | 366 |

<210> SEQ ID NO 8
<211> LENGTH: 324
<212> TYPE: DNA
<213> ORGANISM: Mus sp.

<400> SEQUENCE: 8

| agtattgtga | tgacccagac | tcccaaattc | ctgcttgtct | cagcaggaga | caggattacc | 60 |
| atagcctgca | gggccagtca | gagtgtgagt | aatgatgtag | cttggtacca | acagaagcca | 120 |
| gggcagtctc | ctaaactgct | gataaactat | acatccaatc | gctacactgg | agtccctgat | 180 |
| cgcttcactg | gcagtggata | tgggacggat | ttcactttca | ccatcagcac | tgtgcaggct | 240 |
| gaagacctgg | cagtttattt | ctgtcagcag | gcttatagct | ctccgtggac | gttcggtgga | 300 |
| ggcaccaagc | tggaaatcaa | acgg | | | | 324 |

<210> SEQ ID NO 9
<211> LENGTH: 339
<212> TYPE: DNA
<213> ORGANISM: Mus sp.

<400> SEQUENCE: 9

| gatgtgcagc | ttcaggagtc | gggacctggc | ctggtgaaac | cttctcagtc | tctgtccctc | 60 |
| acctgcactg | tcactggcta | ctcaatcacc | agtgattatg | cctggaactg | gatccggcag | 120 |
| tttccaggaa | acaaactgga | gtggatgggc | tacataagct | acagtgatta | cactagctac | 180 |
| aacccatctc | tcaaaagtcg | aatctctatc | actcgagaca | catccaagaa | ccagttcttc | 240 |
| ctgcagttga | attctgtgac | tactgaggac | acagccacat | attactgtgc | aagaagggtg | 300 |
| gactactggg | gtcaaggaac | ctcagtcacc | gtctcctca | | | 339 |

<210> SEQ ID NO 10
<211> LENGTH: 336
<212> TYPE: DNA
<213> ORGANISM: Mus sp.

<400> SEQUENCE: 10

| gatgttgtga | tgacccaaac | tccactctcc | ctgcctgtca | gtcttggaga | tcaagcctcc | 60 |
| atctcttgca | gatctagtca | gagccttgta | cacagtaatg | gaaacaccta | tttacattgg | 120 |
| tacctgcaga | agccaggcca | gtctccaaag | ctcctgatct | acaaagtttc | caaccgattt | 180 |
| tctggggtcc | cagacaggtt | cagtggcagt | ggatcaggga | cagatttcac | actcaagatc | 240 |
| agcagagtgg | aggctgagga | tctgggagtt | tatttctgct | ctcaaagtac | acatgttccg | 300 | tggacgttcg gtggaggcac cacgctggaa atcaaa                               336

<210> SEQ ID NO 11
<211> LENGTH: 339
<212> TYPE: DNA
<213> ORGANISM: Mus sp.

<400> SEQUENCE: 11
gatgtgcagc ttcaggagtc gggacctggc ctggtgaaac cttctcagtc tctgtccctc     60
acctgcactg tcactggcta ctcaatcacc agtgattatg cctggaactg gatccggcag    120
tttccaggaa acaaactgga gtggatgggc tacataagct tcagtgatag cactagctac    180
aacccatctc tcaaaagtcg aatctctatc actcgagaca catccaagaa ccagttcttc    240
ctgcagttga attctgtgac tactgaggac acagccacat attactgtgc aagaaggggg    300
gactactggg gtcaaggaac ctcagtcacc gtctcctca                           339

<210> SEQ ID NO 12
<211> LENGTH: 336
<212> TYPE: DNA
<213> ORGANISM: Mus sp.

<400> SEQUENCE: 12
gatgttgtga tgacccaaac tccactctcc ctgcctgtca gtcttggaga tcaagcctcc     60
atctcttgca gatctagtca gagccttgta cacagtaatg gaaacaccta tttacattgg    120
tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatcttccg    300
tggacgttcg gtggaggcac caagctggaa atcaaa                              336

<210> SEQ ID NO 13
<211> LENGTH: 113
<212> TYPE: PRT
<213> ORGANISM: Mus sp.

<400> SEQUENCE: 13

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Leu Gly Tyr Ile Ser Phe Asn Asp Asn Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Thr Arg Arg Val Asp Tyr Trp Gly Gln Gly Thr Ser Val Thr Val Ser
            100                 105                 110

Ser

<210> SEQ ID NO 14
<211> LENGTH: 112
<212> TYPE: PRT
<213> ORGANISM: Mus sp.

```
<400> SEQUENCE: 14

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Asn Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 15
<211> LENGTH: 120
<212> TYPE: PRT
<213> ORGANISM: Mus sp.

<400> SEQUENCE: 15

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Val Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Val Phe Ile Ile Thr Ala Phe Asp Tyr Trp Gly Gln
            100                 105                 110

Gly Thr Thr Leu Thr Val Ser Ser
        115                 120

<210> SEQ ID NO 16
<211> LENGTH: 107
<212> TYPE: PRT
<213> ORGANISM: Mus sp.

<400> SEQUENCE: 16

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Ala Asp Tyr Ser Leu Thr Ile Gly Asn Leu Glu Gln
65                  70                  75                  80
```

-continued

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 17
<211> LENGTH: 122
<212> TYPE: PRT
<213> ORGANISM: Mus sp.

<400> SEQUENCE: 17

Gln Val Ser Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Ser Asn Leu Val
65                  70                  75                  80

Phe Leu Lys Ile Thr Ser Val Asp Thr Ala Asp Thr Ala Thr Tyr Tyr
                85                  90                  95

Cys Ala Arg Arg Glu Val Arg Arg Asp Tyr Tyr Ala Met Asp Tyr Trp
            100                 105                 110

Gly Gln Gly Thr Ser Val Thr Val Ser Ser
        115                 120

<210> SEQ ID NO 18
<211> LENGTH: 107
<212> TYPE: PRT
<213> ORGANISM: Mus sp.

<400> SEQUENCE: 18

Ser Ile Val Met Thr Gln Thr Pro Lys Phe Leu Leu Val Ser Ala Gly
1               5                   10                  15

Asp Arg Ile Thr Ile Ala Cys Arg Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Asn Tyr Thr Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Ala Tyr Ser Ser Pro Trp
                85                  90                  95

Thr Phe Gly Gly Gly Thr Lys Leu Glu Ile Lys
            100                 105

<210> SEQ ID NO 19
<211> LENGTH: 113
<212> TYPE: PRT
<213> ORGANISM: Mus sp.

<400> SEQUENCE: 19

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp

-continued

```
                    20                  25                  30

Tyr Ala Trp Asn Trp Ile Arg Gln Phe Pro Gly Asn Lys Leu Glu Trp
            35                  40                  45

Met Gly Tyr Ile Ser Tyr Ser Asp Tyr Thr Ser Tyr Asn Pro Ser Leu
        50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Arg Val Asp Tyr Trp Gly Gln Gly Thr Ser Val Thr Val Ser
            100                 105                 110

Ser

<210> SEQ ID NO 20
<211> LENGTH: 112
<212> TYPE: PRT
<213> ORGANISM: Mus sp.

<400> SEQUENCE: 20

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Thr Leu Glu Ile Lys
            100                 105                 110

<210> SEQ ID NO 21
<211> LENGTH: 113
<212> TYPE: PRT
<213> ORGANISM: Mus sp.

<400> SEQUENCE: 21

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Phe Ser Asp Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Arg Gly Asp Tyr Trp Gly Gln Gly Thr Ser Val Thr Val Ser
            100                 105                 110

Ser
```

<210> SEQ ID NO 22
<211> LENGTH: 112
<212> TYPE: PRT
<213> ORGANISM: Mus sp.

<400> SEQUENCE: 22

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Leu Pro Trp Thr Phe Gly Gly Gly Thr Lys Leu Glu Ile Lys
            100                 105                 110

<210> SEQ ID NO 23
<211> LENGTH: 21
<212> TYPE: DNA
<213> ORGANISM: Artificial
<220> FEATURE:
<223> OTHER INFORMATION: siRNA duplex with 3' dTdT overhang

<400> SEQUENCE: 23
cagacacggc cacgugugatt                                              21

<210> SEQ ID NO 24
<211> LENGTH: 21
<212> TYPE: DNA
<213> ORGANISM: Artificial
<220> FEATURE:
<223> OTHER INFORMATION: siRNA duplex with 3' dTdT overhang

<400> SEQUENCE: 24
ucacacgugg ccgugucugtt                                              21

<210> SEQ ID NO 25
<211> LENGTH: 21
<212> TYPE: DNA
<213> ORGANISM: Artificial
<220> FEATURE:
<223> OTHER INFORMATION: siRNA duplex with 3' dTdT overhang

<400> SEQUENCE: 25
gcuagcgccc auucaauagtt                                              21

<210> SEQ ID NO 26
<211> LENGTH: 21
<212> TYPE: DNA
<213> ORGANISM: Artificial
<220> FEATURE:
<223> OTHER INFORMATION: siRNA duplex with 3' dTdT overhang

<400> SEQUENCE: 26
cuauugaaug ggcgcuagctt                                              21

<210> SEQ ID NO 27

```
<211> LENGTH: 21
<212> TYPE: DNA
<213> ORGANISM: Artificial
<220> FEATURE:
<223> OTHER INFORMATION: siRNA duplex with 3' dTdT overhang

<400> SEQUENCE: 27
gcuuacuccc uucaaacgatt                                                      21

<210> SEQ ID NO 28
<211> LENGTH: 21
<212> TYPE: DNA
<213> ORGANISM: Artificial
<220> FEATURE:
<223> OTHER INFORMATION: siRNA duplex with 3' dTdT overhang

<400> SEQUENCE: 28
ucguuugaag ggaguaagctt                                                      21

<210> SEQ ID NO 29
<211> LENGTH: 21
<212> TYPE: DNA
<213> ORGANISM: Artificial
<220> FEATURE:
<223> OTHER INFORMATION: siRNA duplex with 3' dTdT overhang

<400> SEQUENCE: 29
ccccagagaa auaucugcatt                                                      21

<210> SEQ ID NO 30
<211> LENGTH: 21
<212> TYPE: DNA
<213> ORGANISM: Artificial
<220> FEATURE:
<223> OTHER INFORMATION: siRNA duplex with 3' dTdT overhang

<400> SEQUENCE: 30
ugcagauauu ucucuggggtt                                                      21
```